(12) United States Patent
Inoue et al.

(10) Patent No.: US 10,302,561 B2
(45) Date of Patent: May 28, 2019

(54) LIGHT SOURCE APPARATUS, AND INFORMATION ACQUISITION APPARATUS USING THE SAME

(71) Applicant: CANON KABUSHIKI KAISHA, Tokyo (JP)

(72) Inventors: Yukihiro Inoue, Utsunomiya (JP); Takefumi Ota, Nagareyama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/698,443

(22) Filed: Sep. 7, 2017

(65) Prior Publication Data
US 2018/0073981 A1 Mar. 15, 2018

(30) Foreign Application Priority Data

Sep. 12, 2016 (JP) .................................. 2016-177198
Jul. 28, 2017 (JP) .................................. 2017-146079

(51) Int. Cl.
| | | |
|---|---|---|
| G01B 9/02 | (2006.01) | |
| G01J 3/02 | (2006.01) | |
| G01J 3/10 | (2006.01) | |
| G01J 3/44 | (2006.01) | |
| G02F 1/35 | (2006.01) | |
| G02F 1/39 | (2006.01) | |
| G01N 21/47 | (2006.01) | |
| G01N 21/65 | (2006.01) | |

(52) U.S. Cl.
CPC ..... *G01N 21/4795* (2013.01); *G01B 9/02007* (2013.01); *G01B 9/02044* (2013.01); *G01J 3/0218* (2013.01); *G01J 3/10* (2013.01); *G01J 3/44* (2013.01); *G01N 21/65* (2013.01); *G02F 1/3544* (2013.01); *G02F 1/395* (2013.01); *G01N 2021/655* (2013.01); *G02F 2203/04* (2013.01)

(58) Field of Classification Search
CPC ...................... G02F 2001/3542; H01S 3/0092
See application file for complete search history.

(56) References Cited

U.S. PATENT DOCUMENTS 9,557,626 B2 * 1/2017 Inoue ...................... G02F 1/395
9,880,446 B2 * 1/2018 Gottschall ............. G02F 1/3536
(Continued)

FOREIGN PATENT DOCUMENTS

JP        2015230471 A        12/2015

OTHER PUBLICATIONS

Thomas Gottschall, et al., "Fiber-based Optical Parametric Oscillator for High Resolution Coherent Anti-Stokes Raman Scattering (CARS) Microscopy", Optics Express, Sep. 8, 2014, pp. 21921-21928, vol. 22, No. 18.

(Continued)

*Primary Examiner* — Shawn Decenzo
(74) *Attorney, Agent, or Firm* — Canon U.S.A., Inc. IP Division

(57) ABSTRACT

A center wavelength of first pulsed light (exciting pulsed light) is variable, and a pulse rate of the first pulsed light coincides with an integer multiple of a free spectral interval of an optical oscillator at a center wavelength of second pulsed light (signal pulsed light or idler pulsed light). A center wavelength of a nonlinear gain generated by a nonlinear optical medium is made approximately coincident with the center wavelength of the second pulsed light.

17 Claims, 22 Drawing Sheets

(56) References Cited

U.S. PATENT DOCUMENTS

| | | | | |
|---|---|---|---|---|
| 2012/0188554 A1* | 7/2012 | Inoue | ............. | H01S 3/08013 |
| | | | | 356/479 |
| 2014/0050234 A1* | 2/2014 | Ter-Mikirtychev | ............. | |
| | | | | H01S 3/10007 |
| | | | | 372/6 |
| 2014/0247448 A1* | 9/2014 | Wise | ............. | G01N 21/65 |
| | | | | 356/301 |
| 2015/0015938 A1* | 1/2015 | Kieu | ............. | G02F 1/395 |
| | | | | 359/341.3 |
| 2015/0357786 A1* | 12/2015 | Inoue | ............. | H01S 3/06754 |
| | | | | 250/221 |
| 2016/0231640 A1* | 8/2016 | Inoue | ............. | G02F 1/395 |
| 2016/0377959 A1* | 12/2016 | Inoue | ............. | G02F 1/395 |
| | | | | 359/330 |

OTHER PUBLICATIONS

D. Churin, et al., High power, widely tunable synchronously pumped fiber-based optical parametric oscillator, Conference on Lasers and Electro-Optics, OSA Technical Digest (2016) (Optical Society of America, 2016), paper SW4P.2.

T. N. Nguyen, et al., Widely tunable normal dispersion fiber optical parametric oscillator, CLEO: 2014, OSA Technical Digest (online) (Optical Society of America, 2014), paper SM1O.7.

* cited by examiner

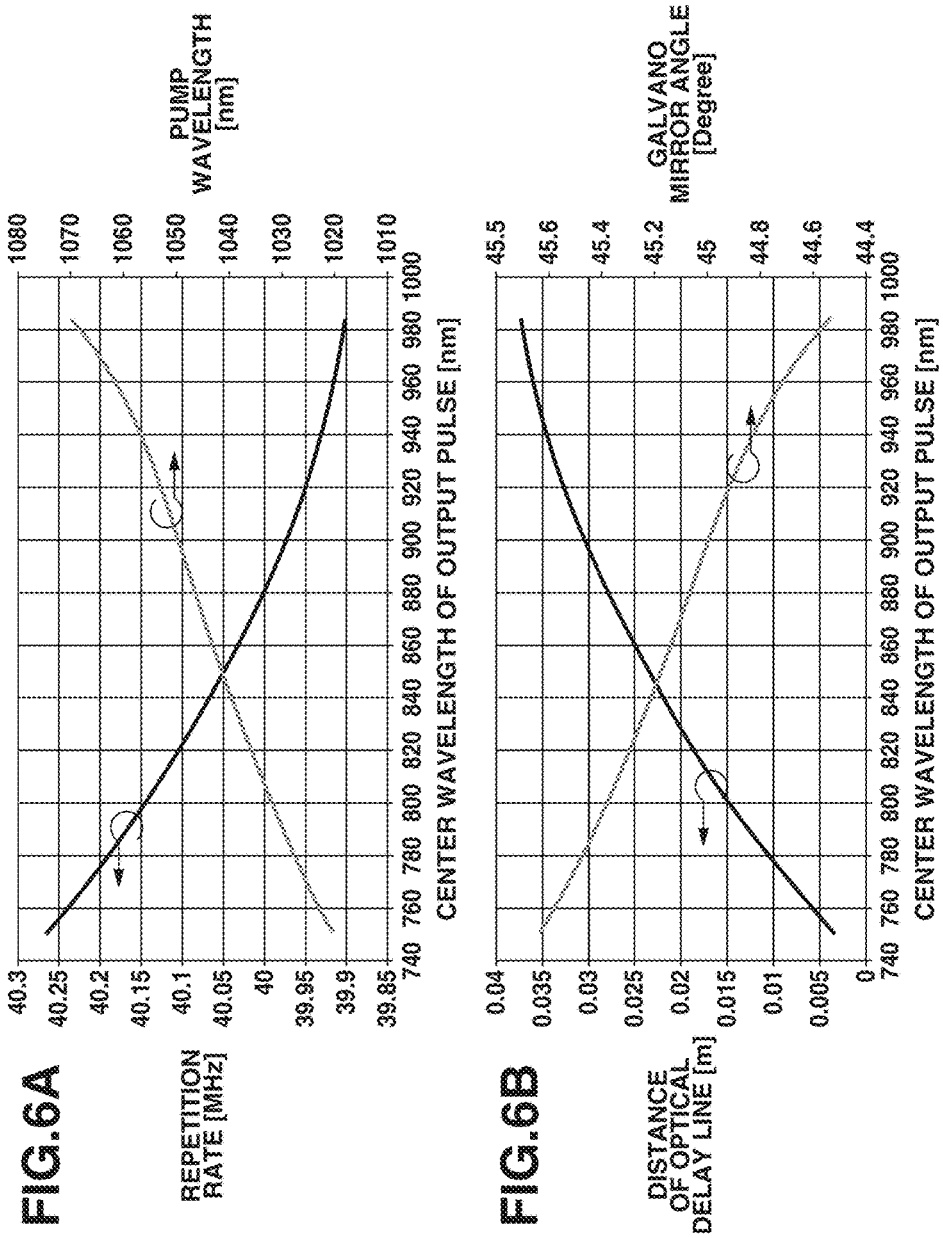

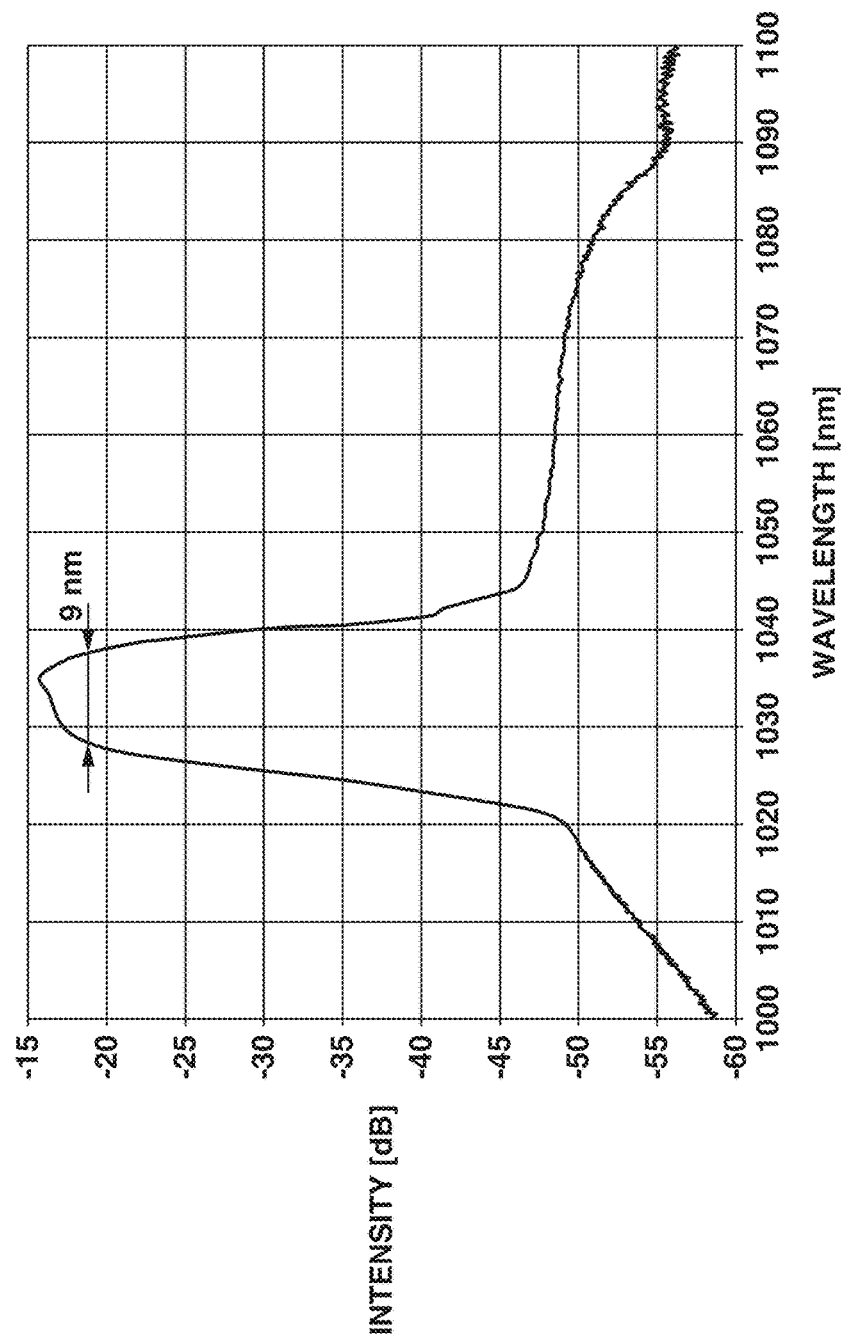

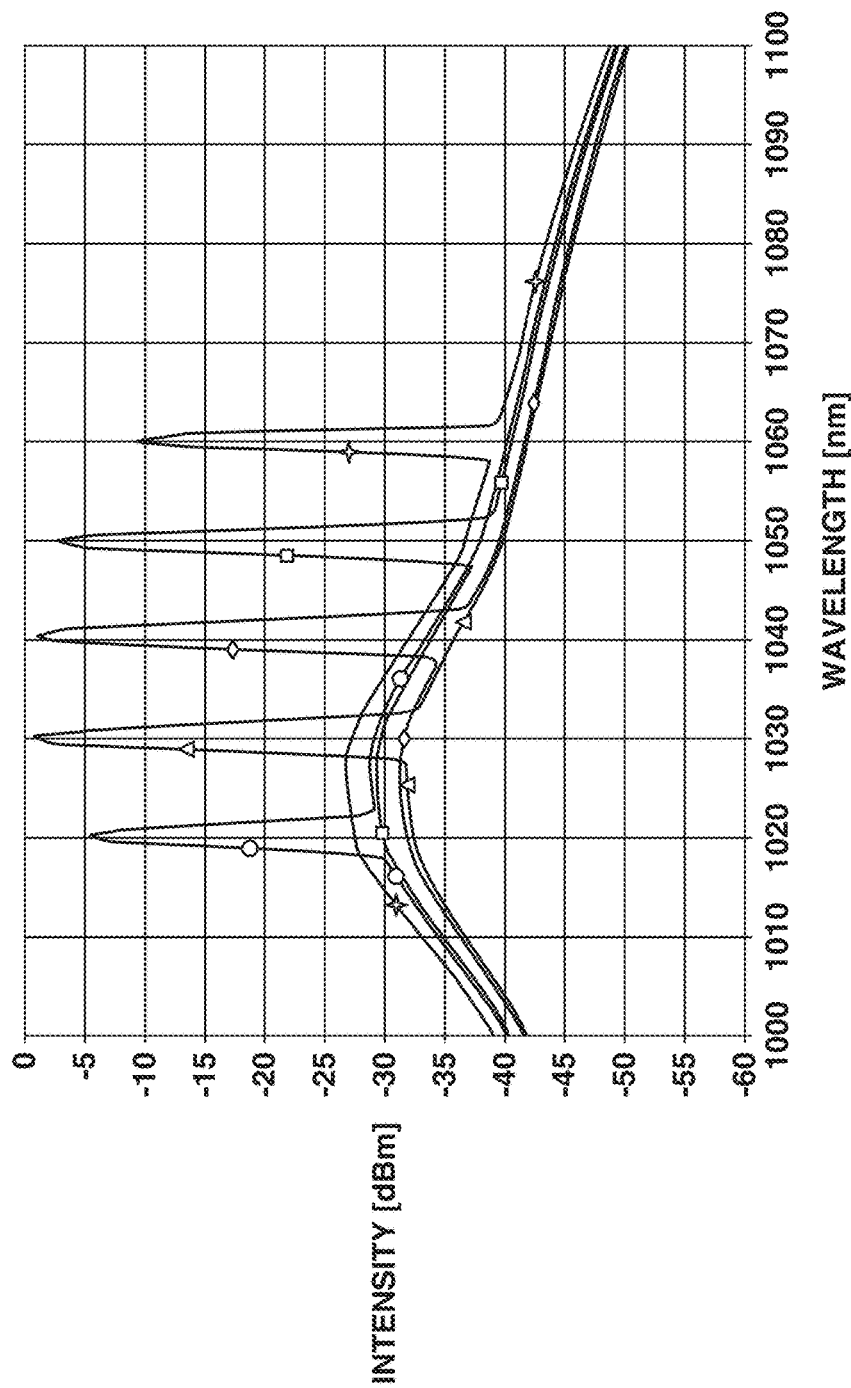

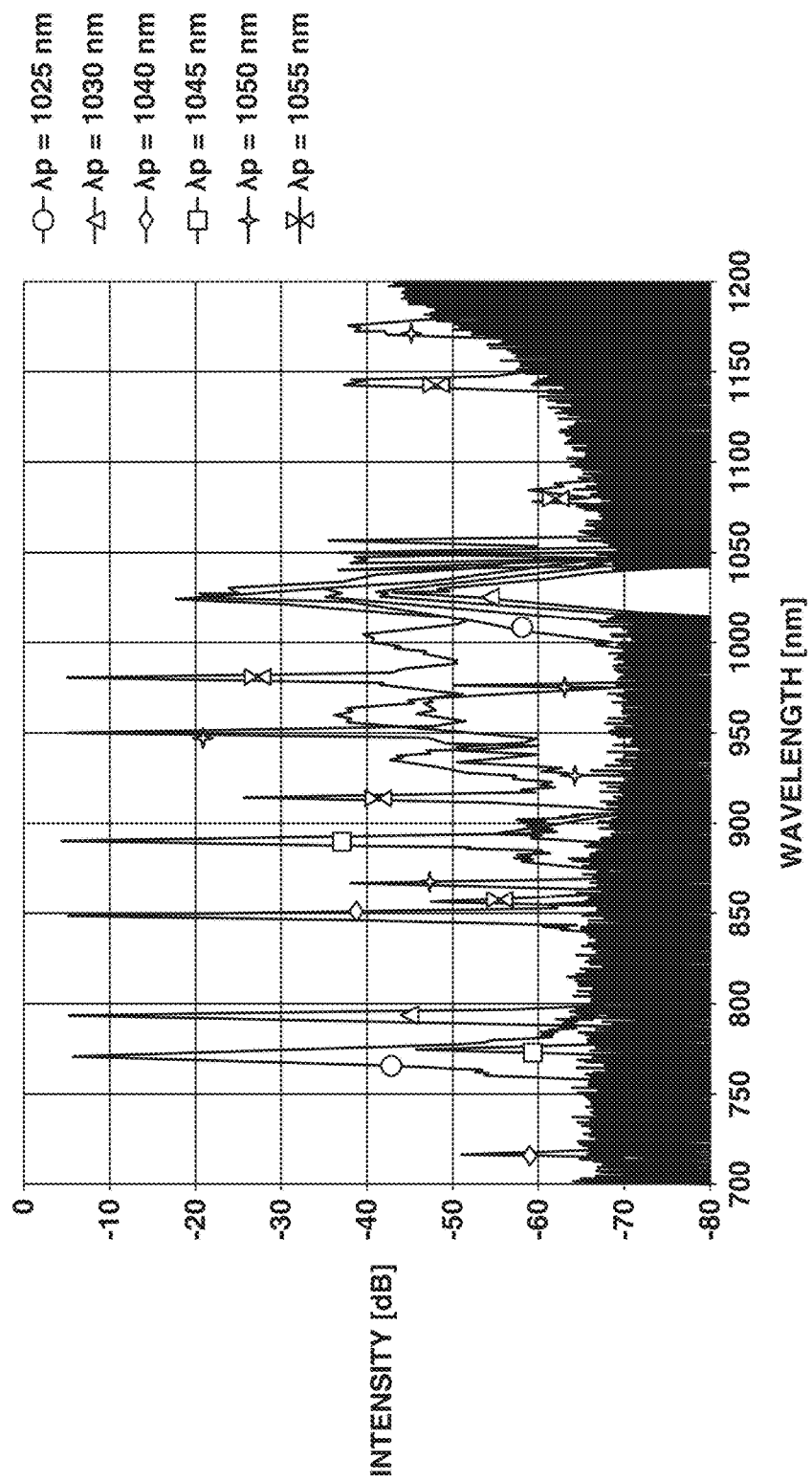

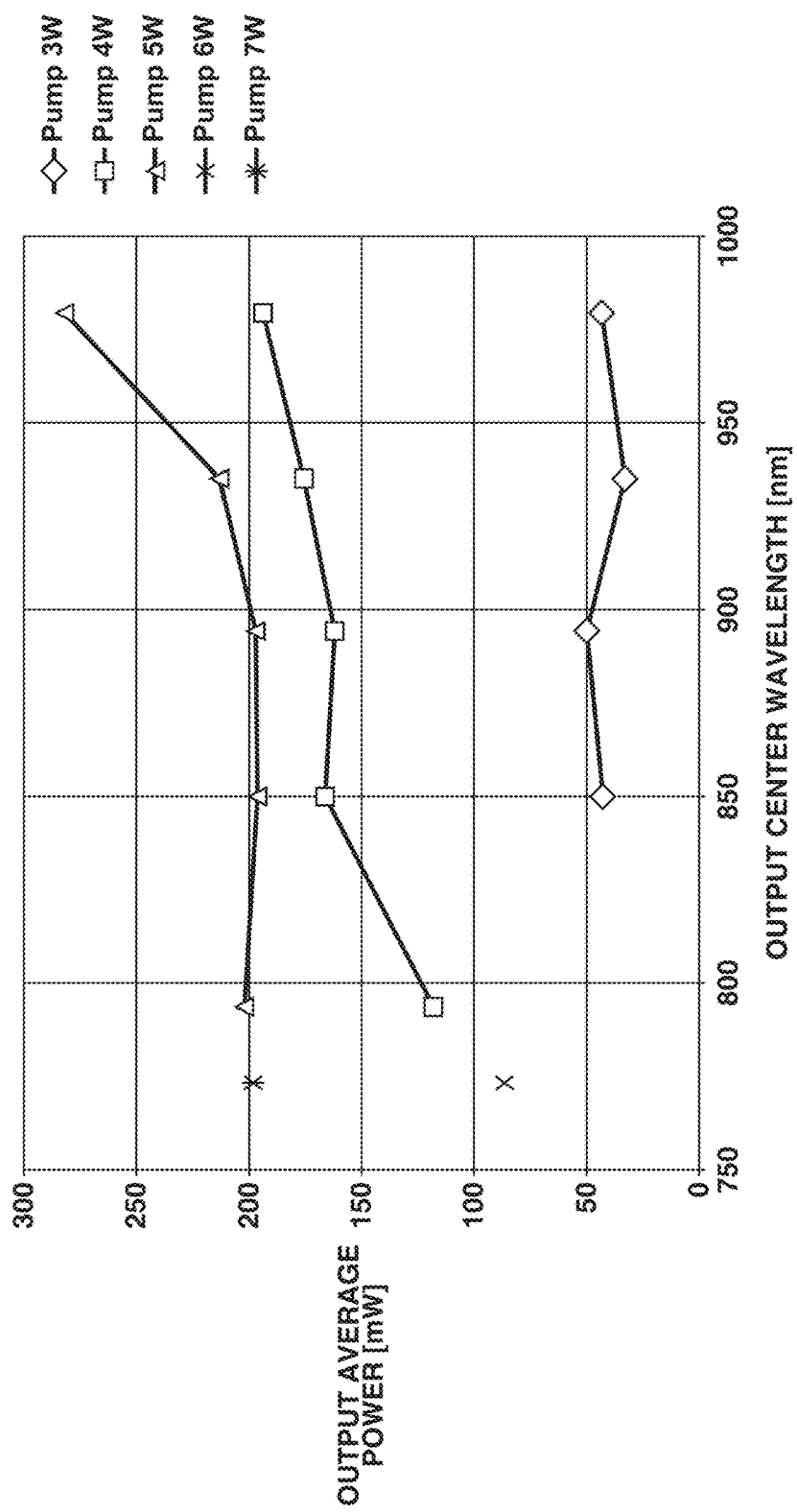

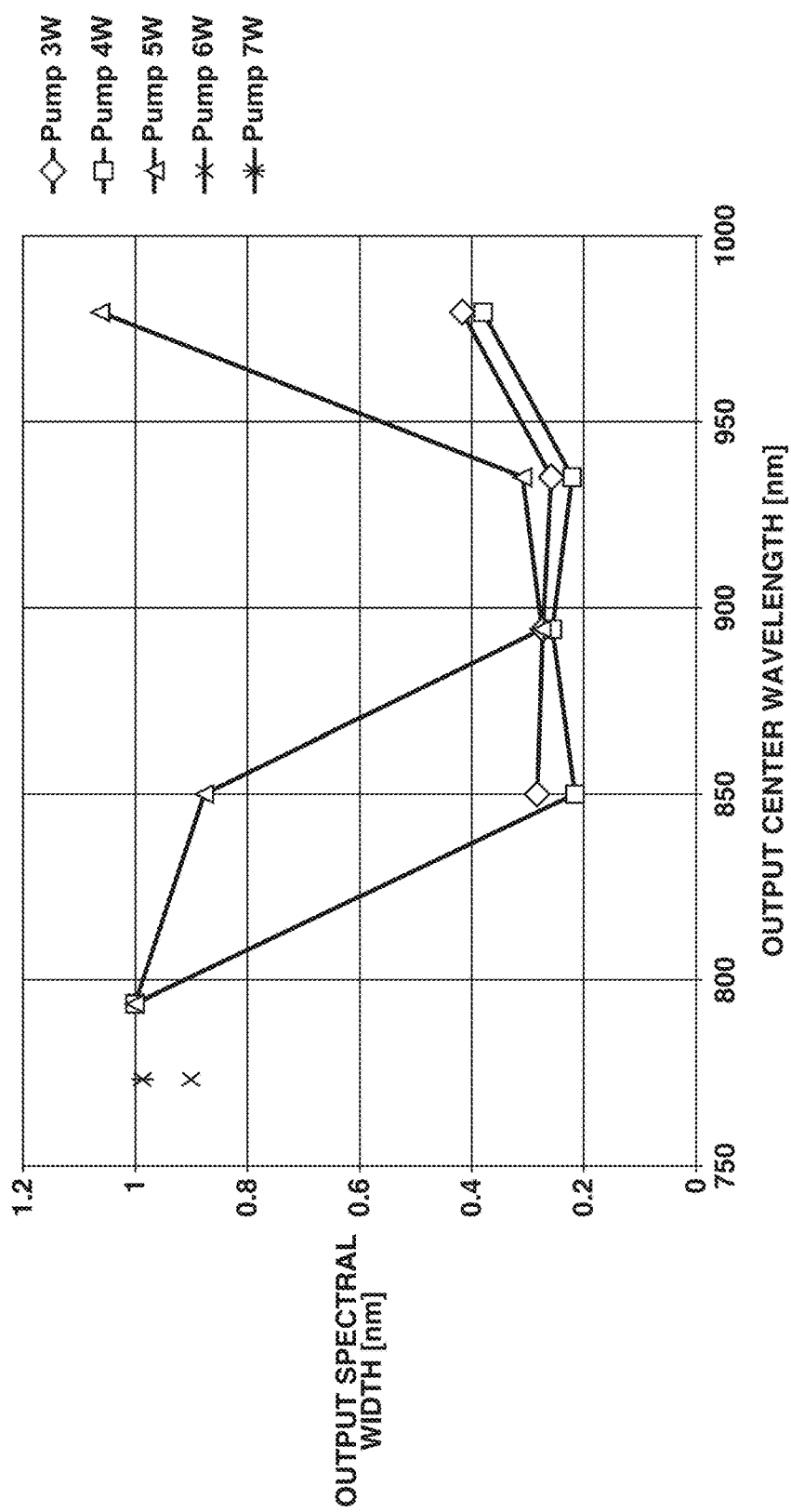

LIGHT SOURCE APPARATUS, AND INFORMATION ACQUISITION APPARATUS USING THE SAME

BACKGROUND OF THE INVENTION

Field of the Invention

The present invention relates to a light source apparatus having, in particular, a light source that emits pulsed light of which center wavelength is variable, and an information acquisition apparatus using the light source apparatus.

Description of the Related Art

A variety of information on constituent materials of an object can be obtained by irradiating the object with pulsed light and detecting light reflected and scattered by the object, light transmitted through the object, or fluorescence emitted from the object. In recent years, identification of a substance of an object has been researched using the following method: an object is irradiated with two pulsed light beams having a frequency difference corresponding to a molecular vibration frequency, and light generated in the object due to Stimulated Raman Scattering (SRS) and Coherent Anti-Stokes Raman Scattering (CARS) is detected.

As a laser beam source that generates two pulsed light beams having center wavelengths different from each other, a fiber optical parametric oscillator (FOPO) is known. The fiber optical parametric oscillator uses four wave mixing (a kind of optical parametric effect) that occurs in a nonlinear optical fiber. In FOPO, upon reception of power of exciting pulsed light incident on an optical fiber, pulsed light with a wavelength different from that of the exciting pulsed light is generated, and the generated pulsed light is oscillated in the oscillator.

More specifically, when an exciting pulsed light is incident on a nonlinear optical fiber arranged in the FOPO, pulsed light (signal pulsed light) with a wavelength shorter than that of the exciting pulsed light and pulsed light (idler pulsed light) with a wavelength longer than that of the exciting pulsed light are simultaneously generated. A portion of the signal pulsed light or idler pulsed light is fed back and then is guided again to the oscillator synchronously with pump pulsed light to be oscillated. The signal pulsed light, the idler pulsed light, or both of them is/are taken out as an output.

In "Optics Express Vol. 22, No. 18, pp. 21921-21928, 8 Sep. 2014", there is disclosed a method in which a center wavelength of exciting pulsed light is fixed, and a portion for adjusting the length of an optical path is disposed in an optical oscillator to change an oscillation frequency. The center wavelength of signal pulsed light is changed in a FOPO.

In the above "Optics Express", the center wavelength of exciting pulsed light is fixed, and therefore the center wavelength of optical parametric gain is also fixed. Accordingly, a wavelength variable range of oscillated signal pulsed light is limited within range of optical parametric gain. Therefore, the range is narrow, and light intensity varies in the wavelength variable range and is not constant. Since the center wavelength of optical parametric gain is changed by changing the center wavelength of exciting pulsed light, the wavelength variable range of the signal pulsed light can be broadened. However, in a case where the center wavelength of optical parametric gain does not coincide with the center wavelength of oscillated signal pulsed light, the following phenomenon may occur: when the center wavelength of signal pulsed light is changed, the light intensity of the signal pulsed light is likely to vary owing to the above-described change in the center wavelength.

SUMMARY OF THE INVENTION

According to an aspect of the present invention, in the light of the above problem, a light source apparatus includes a light source portion configured to emit first pulsed light, an optical oscillator including a nonlinear optical medium for generating second pulsed light with a wavelength different from a wavelength of the first pulsed light upon incidence of the first pulsed light on the medium, a light branch portion configured to branch and output the second pulsed light, a light combining portion configured to guide the second pulsed light to the optical oscillator and guide the first pulsed light to the optical oscillator, a center wavelength adjustment portion configured to adjust a center wavelength of the first pulsed light; and a pulse rate adjustment portion configured to perform adjustment such that a pulse rate of the first pulsed light coincide with an integer multiple of a free spectral interval of the optical oscillator at a center wavelength of the second pulsed light, wherein a center wavelength of a nonlinear gain generated by the nonlinear optical medium is made approximately coincident with the center wavelength of the second pulsed light.

Further features of the present invention will become apparent from the following description of exemplary embodiments with reference to the attached drawings.

BRIEF DESCRIPTION OF THE DRAWINGS

FIG. 6A is a graph illustrating the relationship among an output wavelength of the FOPO, a repetition rate, and a pump light wavelength, and FIG. 6B is a graph illustrating the relationship among the output wavelength of the FOPO, a delay amount of the optical delay device, and an angle of the galvano mirror.

FIG. 17 is a graph illustrating a measurement result of spectrum of pulsed light emitted from the seed light source.

FIG. 19 is a graph illustrating a measurement result of spectrum of pulsed light emitted from a port while a center wavelength is changed at each interval of 10 nm in a range between 1020 nm and 1060 nm.

FIG. 20 is a graph illustrating measurement result of spectrum of pulsed light at a time when a short wavelength transmission filter for selecting light at a wavelength shorter than 990 nm is used.

FIG. 21 is a graph in which output power at each wavelength shown FIG. 20 is plotted.

FIG. 22 is a graph in which spectral width at each wavelength shown FIG. 20 is plotted.

DESCRIPTION OF THE EMBODIMENTS

Figure 1:
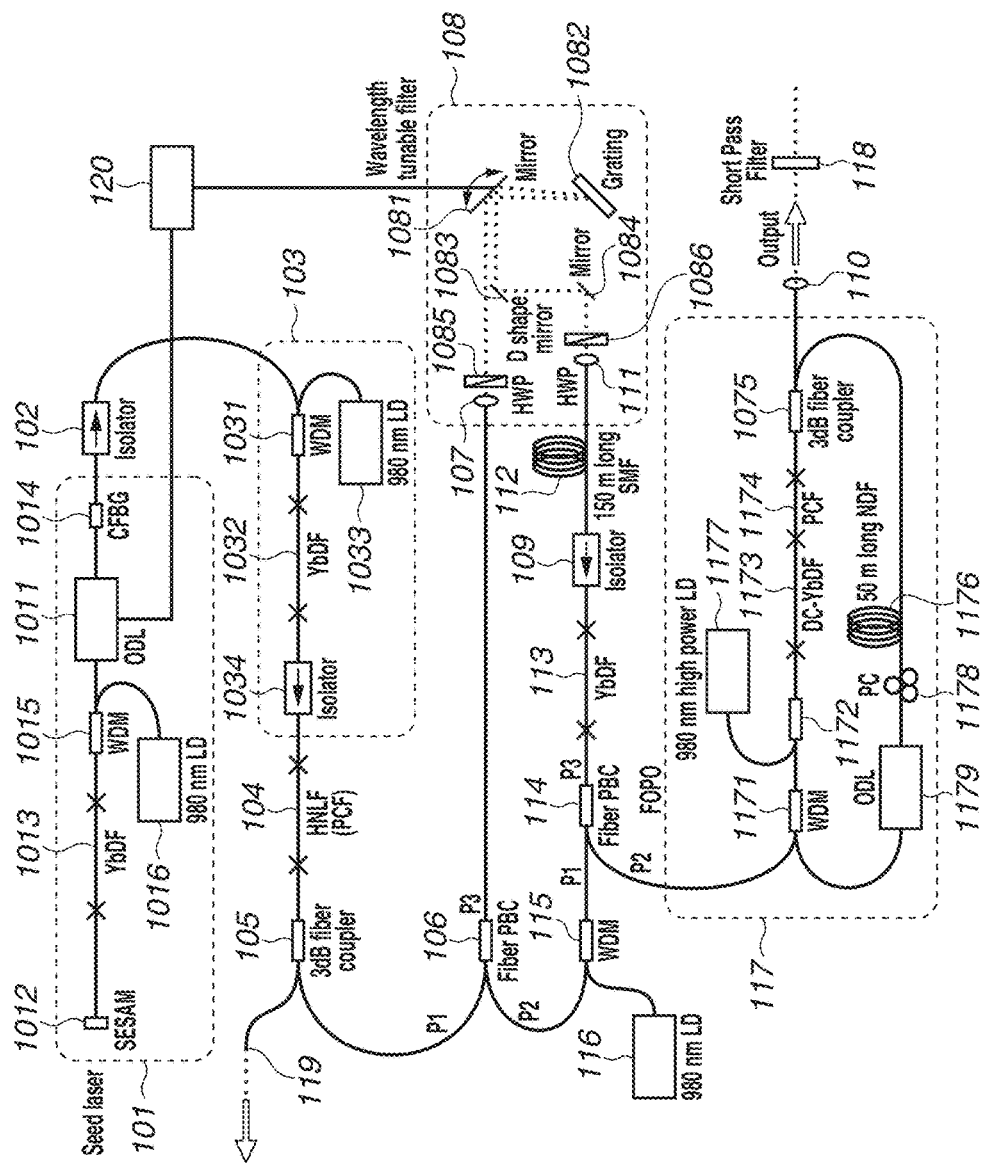
FIG. 1 is a schematic view illustrating a light source apparatus according to first and second exemplary embodiments of the present invention.

A light source apparatus according to one aspect of the present invention includes a light source portion for emitting exciting pulsed light with a variable center wavelength, and a nonlinear optical medium for generating signal pulsed light. The nonlinear optical medium is provided in an optical oscillator for oscillating the signal pulsed light. As the nonlinear optical medium, an optical fiber can be preferably used. When the exciting pulsed light emitted from the light source portion is input into the nonlinear optical medium, the signal pulsed light with a wavelength different from that of the exciting pulsed light is generated owing to an optical parametric gain that is a nonlinear gain of the nonlinear optical medium. Upon a slight change in the center wavelength of the exciting pulsed light, the center wavelength of the optical parametric gain is largely changed. Therefore, the center wavelength of the signal pulsed light generated owing to the optical parametric gain is largely changed. Using this phenomenon, the light source apparatus can change a wavelength difference between two emission pulsed light beams in a broad band region. Here, two pulsed light beams are those emitted from the nonlinear optical medium. However, as the two pulsed light beams, a pulsed light beam branching from the exciting pulsed light and the other pulsed light beam selected from the pulsed light emitted from the nonlinear optical medium can similarly be used, for example.

Further, in order to laser-oscillate the signal pulsed light generated in the nonlinear optical medium, it is necessary to make a pulse rate of the exciting pulsed light equal to an integer multiple of a free spectral interval of the optical oscillator at the center wavelength of the signal pulsed light. To paraphrase the above, it is necessary to make a time point of irradiation of the nonlinear optical medium with the exciting pulsed light coincident with a time point of incidence of the signal pulsed light on the nonlinear optical medium after circulation of the signal pulsed light through the optical oscillator. Thus, the signal pulsed light can be laser-oscillated, and the light intensity of the signal pulsed light can be increased.

However, where the center wavelength of the optical parametric gain is not coincident with the center wavelength of the laser-oscillated signal pulsed light, the light intensity of the signal pulsed light varies depending on the center wavelength of the signal pulsed light when the center wavelength of the signal pulsed light is changed. According to the present invention, when the center wavelength of the signal pulsed light is changed, the center wavelength of the optical parametric gain and the center wavelength the signal pulsed light are made approximately coincident with each other by a center wavelength adjustment portion. Hence, the light intensity of the signal pulsed light can be made constant irrespective of the center wavelength of the signal pulsed light.

Before exemplary embodiments of the present invention will be described in detail, a generation principle of four wave mixing will be described. The four wave mixing is an origin of optical parametric gain for generating signal pulsed light from exciting pulsed light.

The four wave mixing is a phenomenon that when two beams (exciting pulsed light beams) with frequencies (wavelengths) different from each other is input into the nonlinear optical medium, such as an optical fiber, new light is generated at a wavelength different from those of the two exciting pulsed light beams. Here, a portion of power of light incident on the optical fiber is transferred to power of the new light generated due to the four wave mixing. For example, assumed that two light beams at frequencies $\omega_1$ and $\omega_2$ are incident on the nonlinear optical medium, and two light beams at frequencies $\omega_3$ and $\omega_4$ are newly generated, respectively, and then the relationship of $\omega_1+\omega_2=\omega_3+\omega_4$ is satisfied.

Where the frequency of incidence light (exciting pulsed light) is one, that is, $\omega_1=\omega_2=\omega_c$, the phenomenon is called degenerate four wave mixing. Two light beams at frequencies of $\omega_c+\Delta\omega$ and $\omega_c-\Delta\omega$, which are symmetrical with respect to $\omega_c$, is generated. Generally, light on a higher frequency side is called signal pulsed light, and light on a lower frequency side is called idler pulsed light. Hereinafter, a frequency of the signal pulsed light is represented by $\omega_{s1}$ ($=\omega_c+\Delta\omega$), and a frequency of the idler pulsed light is represented by $\omega_{s2}$ ($=\omega_c-\Delta\omega$).

Compared with a case where two light beams with frequencies different from each other are incident, the degenerate four wave mixing is simple in wavelength control and in its structure. Therefore, the degenerate four wave mixing is widely employed in a light source of an information acquisition apparatus using SRS and CARS. The degenerate four wave mixing will be described.

In order to efficiently generate the degenerate four wave mixing, a phase matching condition represented by the following formula (1) should be satisfied:

$$-4\gamma P_c < \Delta\beta = \beta_{s1} + \beta_{s2} - 2\beta_c < 0 \quad \gamma = \frac{\omega_c}{c}\frac{n_2}{A_{\text{eff}}}, \quad (1)$$

where $\beta_c$ is a propagation constant of the exciting pulsed light incident on the nonlinear optical medium, $\beta_{s1}$ is a propagation constant of the signal pulsed light, and $\beta_{s2}$ is a propagation constant of the idler pulsed light. Further, $\Delta\beta$ is phase mismatching between propagation constants of the light beams in the nonlinear optical medium, $\gamma$ is a nonlinear factor of the nonlinear optical medium, and $P_c$ is a peak intensity of the exciting pulsed light. Furthermore, $n_2$ is a nonlinear refractive index of the nonlinear optical medium, $A_{\text{eff}}$ is an effective sectional area of a core in the optical fiber that is nonlinear optical medium, and c is the velocity of light in vacuum. The phase mismatching $\Delta\beta$ between propagation constants of light in the nonlinear optical medium can be represented by the following formula (2) using the frequency difference $\Delta\omega$:

$$\Delta\beta = \beta_2(\Delta\omega)^2 + \beta_4(\Delta\omega)^4/12 \quad (2),$$

where $\beta_2$ is a group velocity dispersion at a frequency of the exciting pulsed light in the nonlinear optical medium, and $\beta_4$ is a second derivative of the group velocity dispersion $\beta_2$. The group velocity dispersion $\beta_2$ is a second derivative of the propagation constant $\beta_c$ of the exciting pulsed light. Here, the optical parametric gain G can be represented by the following formula (3):

$$G = \left|\frac{\sinh\left(\sqrt{1-(1+\Delta\beta/2\gamma P_c)^2}\,\gamma P_c L\right)}{\sqrt{1-(1+\Delta\beta/2\gamma P_c)^2}}\right|^2 \quad (3)$$

where L is a length of the nonlinear optical medium.

With respect to four cases where $\beta_2$ is positive or negative and $\beta_4$ is positive or negative, graphs of formula (2) and formula (3) are respectively illustrated in FIGS. 13A and 13B to 16A and 16B.

Figure 13A:
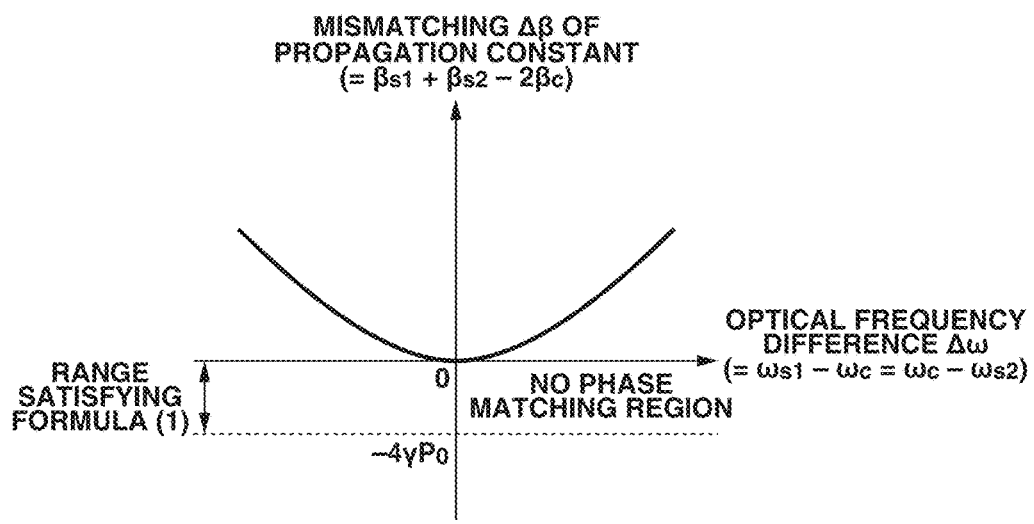
FIGS. 13A and 13B are graphs illustrating a phase mismatching $\Delta\beta$ of light propagation constant in a nonlinear optical medium with $\beta_2>0$ and $\beta_4>0$, and optical parametric gain G.
Figure 13B:
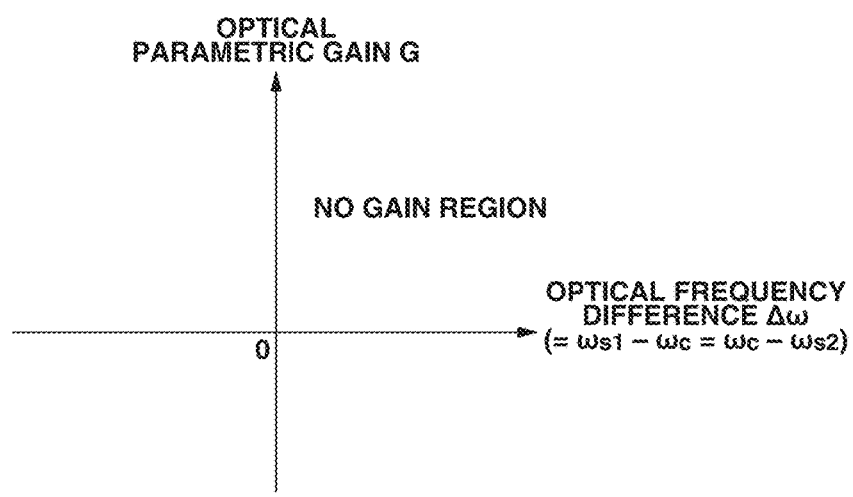

FIGS. 13A and 13B illustrate the case where $\beta_2>0$ and $\beta_4>0$. FIG. 13A shows a graphical representation of formula (2). The axis of ordinate is $\Delta\beta$, and the axis of abscissa is $\Delta\omega$. FIG. 13B shows a graphical representation of formula (3). The axis of ordinate indicates G, and the axis of abscissa indicates $\Delta\omega$. Graphs in FIGS. 14A and 14B to 16A and 16B are similar to the above. Under a phase matching condition of $\Delta\beta$ represented by formula (1), the nonlinear factor $\gamma$ is positive and the peak intensity $P_c$ of the exciting pulsed light is positive. Therefore, $\Delta\beta$ has a negative value.

As is apparent from FIG. 13A, there is not a region satisfying formula (1) when $\beta_2>0$ and $\beta_4>0$. That is, the optical parametric gain G represented by formula (3) cannot be obtained. In such a nonlinear optical medium, even when the exciting pulsed light is incident thereon, neither signal pulsed light nor idler pulsed light can be generated.

Figure 14A:
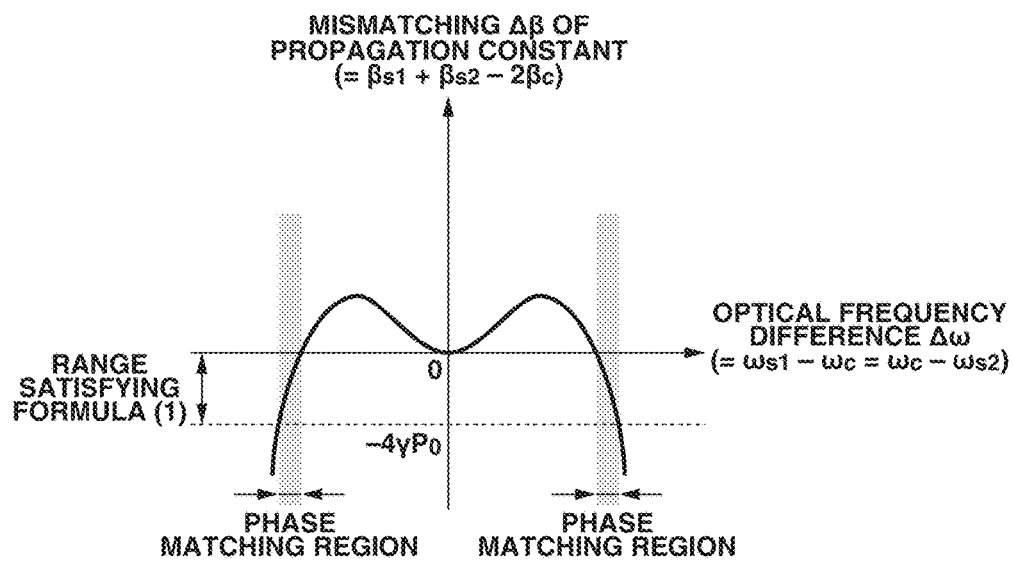
FIGS. 14A and 14B are graphs illustrating a phase mismatching $\Delta\beta$ of light propagation constant in a nonlinear optical medium with $\beta_2>0$ and $\beta_4<0$ and optical parametric gain G.
Figure 14B:
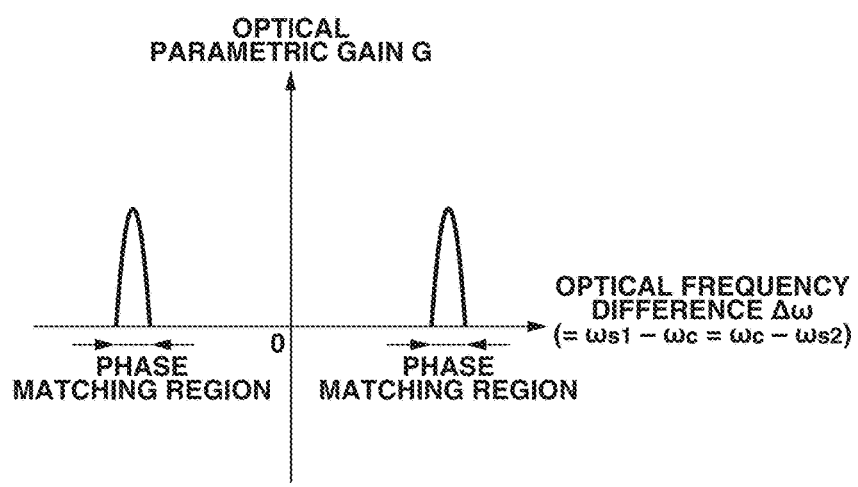

FIGS. 14A and 14B illustrate the case where $\beta_2>0$ and $\beta_4<0$. In the graph of FIG. 14A, hatched portions indicate ranges satisfying the phase matching condition of $\Delta\beta$ represented by formula (1). As is known from this graph, the ranges of $\Delta\omega$ satisfying the phase matching condition represented by formula (1) exist in relatively narrow regions that are remote from the frequency of the exciting pulsed light. Accordingly, as shown in FIG. 14B, when the exciting pulsed light at a given frequency is incident on the nonlinear optical medium, signal pulsed light and idler pulsed light are each generated in narrow frequency band regions since the optical parametric gain G appears in a relatively narrow frequency band region.

Figure 15A:
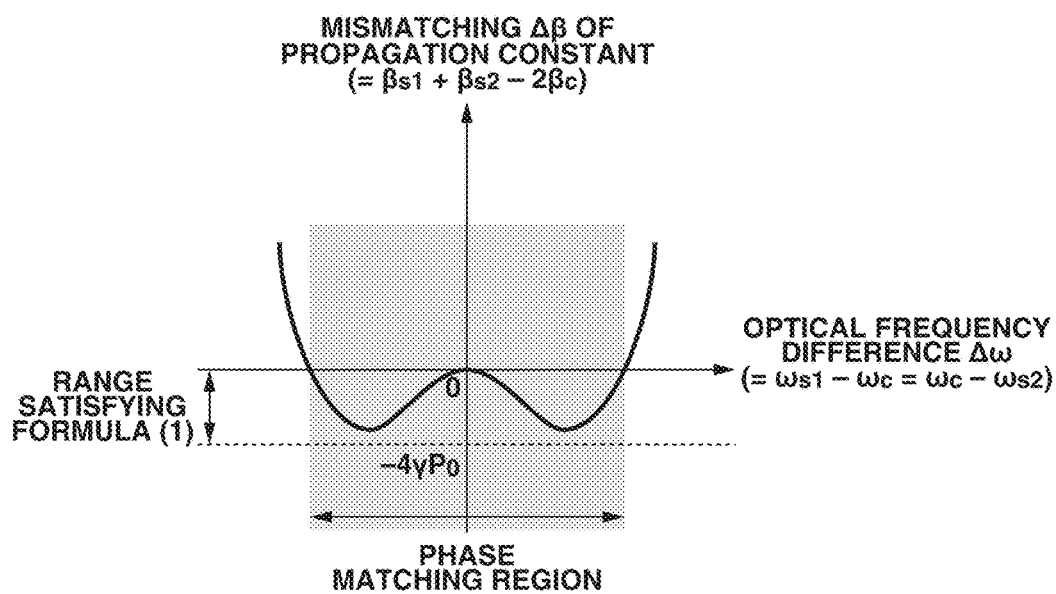
FIGS. 15A and 15B are graphs illustrating a phase mismatching $\Delta\beta$ of light propagation constant in a nonlinear optical medium with $\beta_2<0$ and $\beta_4>0$ and optical parametric gain G.
Figure 15B:
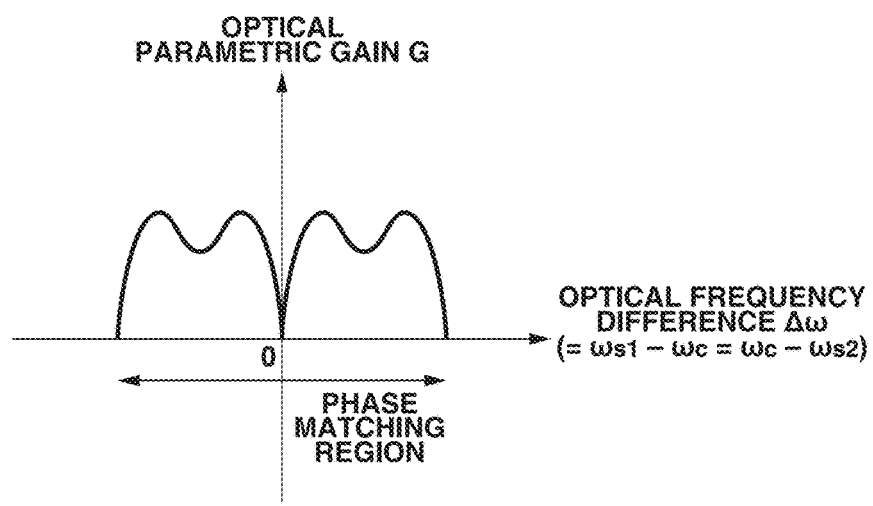
Figure 16A:
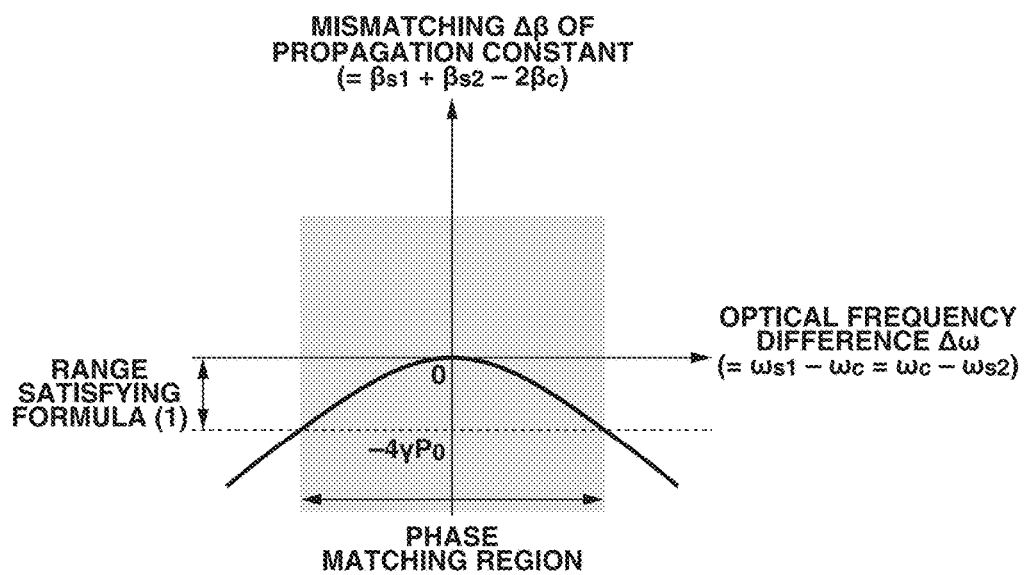
FIGS. 16A and 16B are graphs illustrating a phase mismatching $\Delta\beta$ of light propagation constant in a nonlinear optical medium with $\beta_2<0$ and $\beta_4<0$ and optical parametric gain G.
Figure 16B:
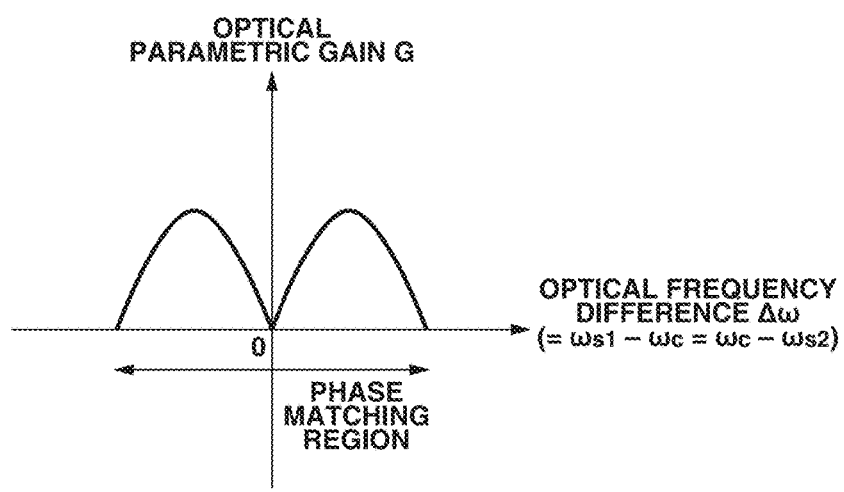

FIGS. 15A and 15B illustrate the case where $\beta_2<0$ and $\beta_4>0$, and FIGS. 16A and 16B illustrate the case where $\beta_2<0$ and $\beta_4<0$. As illustrated in FIGS. 15A and 16A, when the exciting pulsed light is operated in a region of $\beta_2<0$ (anomalous dispersion region), the range of $\Delta\omega$ satisfying the phase matching condition represented by formula (1) is relatively broad. That is, as is shown in FIGS. 15B and 16B, when the pulsed light at a given frequency is incident on the nonlinear optical medium, the optical parametric gain G appears in a relatively broad frequency band region. Hence, signal pulsed light and idler pulsed light are generated over a broad frequency band region.

Accordingly, in order to generate the pulsed light with a narrow spectral line width using the degenerate four wave mixing, a nonlinear optical medium satisfying $\beta_2>0$ and $\beta_4<0$ is used. Such a nonlinear optical medium can be obtained by using the following optical fibers. In the optical fiber, core material and clad material are selected such that a refractive-index difference between the core and the clad has an appropriate value, or the shape of the optical fiber is appropriately designed.

A frequency shift amount $\Delta\omega$ (wavelength shift amount $\Delta\lambda$) of optical parametric gain G, dependent on the exciting pulsed light, generated owing to the degenerate four wave mixing and a frequency width $\delta\omega$ (spectral half width $\delta\lambda$) of the optical parametric gain G can be represented by the following formulae, respectively.

$$\Delta\omega = \sqrt{\frac{12\beta_2}{|\beta_4|}} = \sqrt{\frac{12\beta_3(\omega_c-\omega_0)}{|\beta_4|}} \quad (4)$$

$$\Delta\lambda = \frac{1}{A}\sqrt{\frac{12\beta_2}{|\beta_4|}} = \frac{1}{A}\sqrt{\frac{12\beta_3 A(\lambda_0-\lambda_c)}{|\beta_4|}} \quad A = \frac{2\pi c}{\lambda_0^2} \quad (5)$$

$$\delta\omega = \frac{24\gamma P_c}{|\beta_4|\Delta\omega^3} \quad (6)$$

$$\delta\lambda = \frac{24\gamma P_c}{A^4|\beta_4|\Delta\lambda^3} \quad (7)$$

In the above formulae, $\omega_0$ is a zero dispersion frequency of nonlinear optical medium, $\lambda_c$ is a center wavelength of exciting pulsed light, $\lambda_0$ is a zero dispersion wavelength of nonlinear optical medium, and $\beta_3$ is a first derivative of group velocity dispersion $\beta_2$ at the zero dispersion wavelength. As is known from formula (5), when the center wavelength $\lambda_c$ of the exciting pulsed light is slightly changed, the wavelength of signal pulsed light (or idler pulsed light) can be largely changed by an amount of factor of formula (5). Further, as is known from formula (7), when nonlinear optical medium with a small nonlinear factor $\gamma$ and $\beta_4$ having a large value is used, it is possible to generate signal pulsed light (or idler pulsed light) with a narrow spectral line width $\delta\lambda$. Either or both of signal pulsed light and idler pulsed light can be employed.

Figure 9:
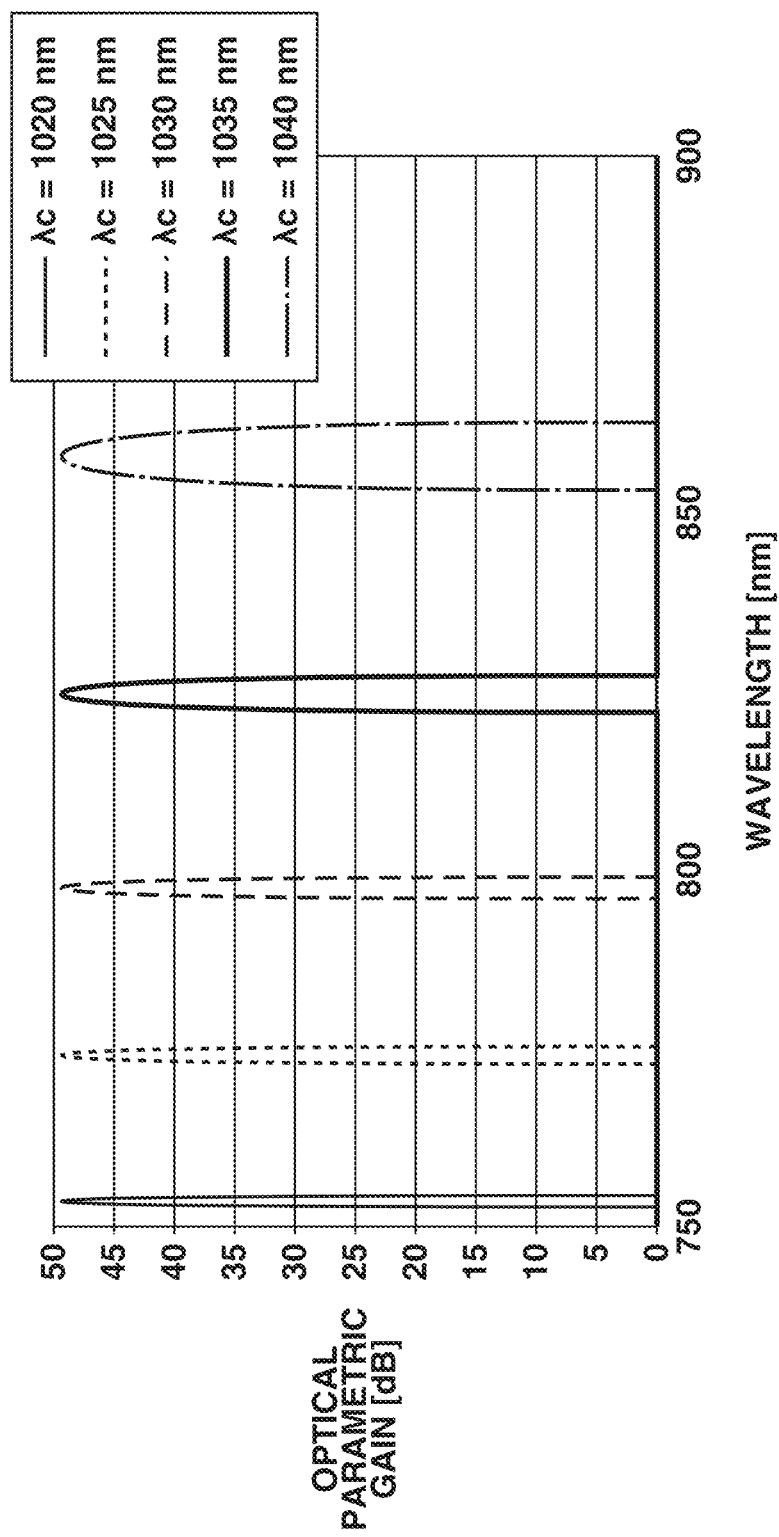
FIG. 9 is a view illustrating a change in optical parametric gain at a time when a center wavelength of exciting pulsed light is changed.
Figure 10:
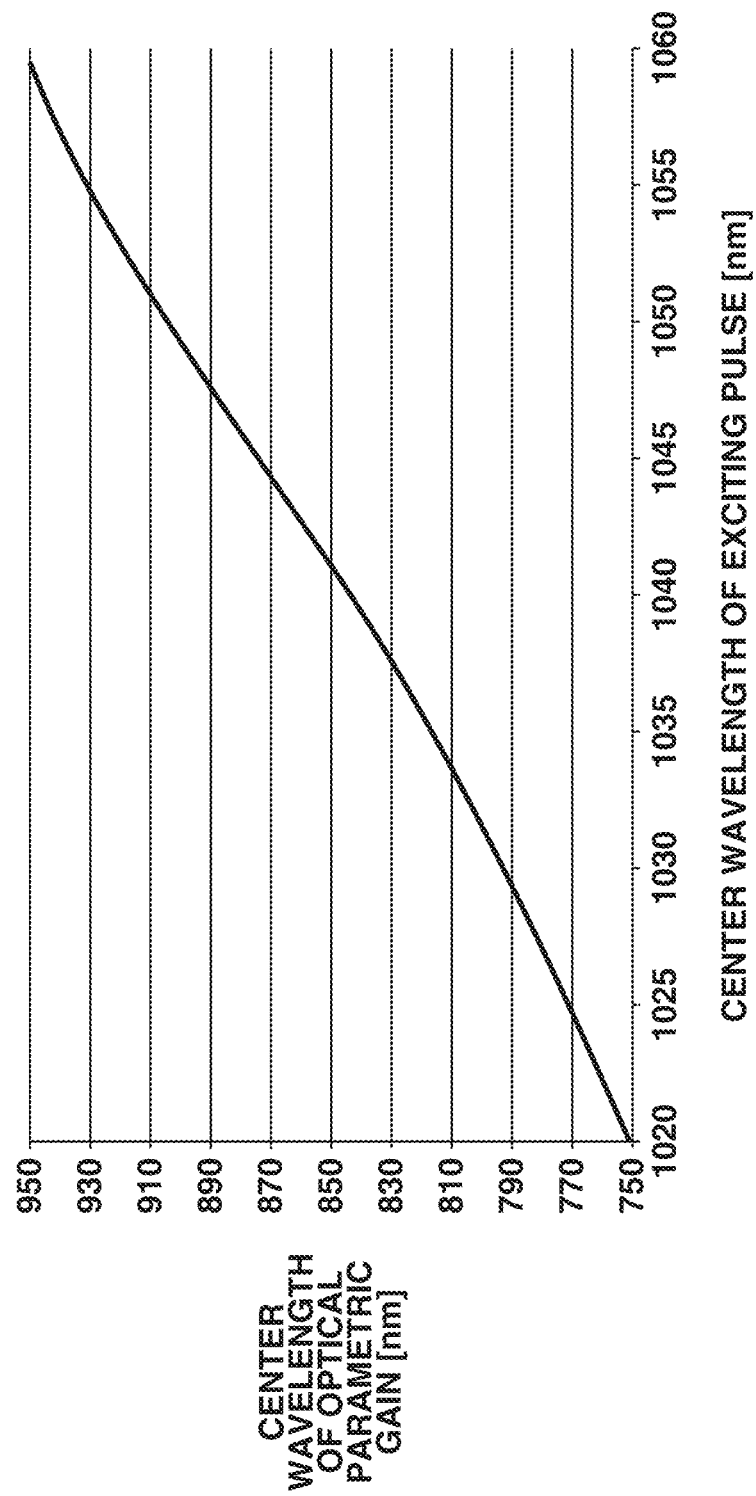
FIG. 10 is a graph illustrating the relationship between a center wavelength of exciting pulsed light, and a center wavelength of optical parametric gain.

Principle for maintaining the intensity of signal pulsed light constant irrespective of the center wavelength of the signal light will be described. FIG. 9 illustrates a changing manner of the optical parametric gain appearing when the center wavelength $\lambda_c$ of the exciting pulsed light is changed. FIG. 9 shows a graph in which G represented by formula (3) is plotted along the axis of ordinate. Here, $P_c=1$ kW, L=0.5 m, and values of $\gamma$, $\lambda_0$, $\beta_2$, $\beta_3$, and $\beta_4$ are those of a photonic crystal fiber (LMA-PM5, NKT made by Photonics Inc.) that is general as the nonlinear optical medium. Further, FIG. 10 illustrates a change of the center wavelength of the optical parametric gain appearing when the center wavelength of the exciting pulsed light changes. As illustrated in FIG. 10, the center wavelength of the optical parametric gain varies in a nonlinear manner when the center wavelength of the exciting pulsed light changes.

On the other hand, in order to generate laser-oscillation of signal pulsed light in an optical oscillator with the nonlinear optical medium, it is necessary to make a time point at which the nonlinear optical medium is irradiated with exciting pulsed light coincident with a time point at which signal pulsed light is again incident on the nonlinear optical medium after circulation of the signal pulsed light through the optical oscillator. That is, as is represented by formula (8), it is necessary to make the pulse rate of exciting pulsed light equal to an integer multiple of the free spectral interval of the optical oscillator at the center wavelength of signal pulsed light:

$$f_c = N * c/(n(\lambda)L) \tag{8}$$

where $f_c$ is the pulse rate of exciting pulsed light, $n(\lambda)$ is a refractive index of the overall optical oscillator containing the nonlinear optical medium, L is a cavity length of the optical oscillator containing the nonlinear optical medium, c is the velocity of light, and N is a natural number.

As is known from the above, when the center wavelength of signal pulsed light is changed, it is necessary to change the pulse rate of exciting pulsed light (or the cavity length of the optical oscillator), and satisfy formula (8) at all times.

Figure 11:
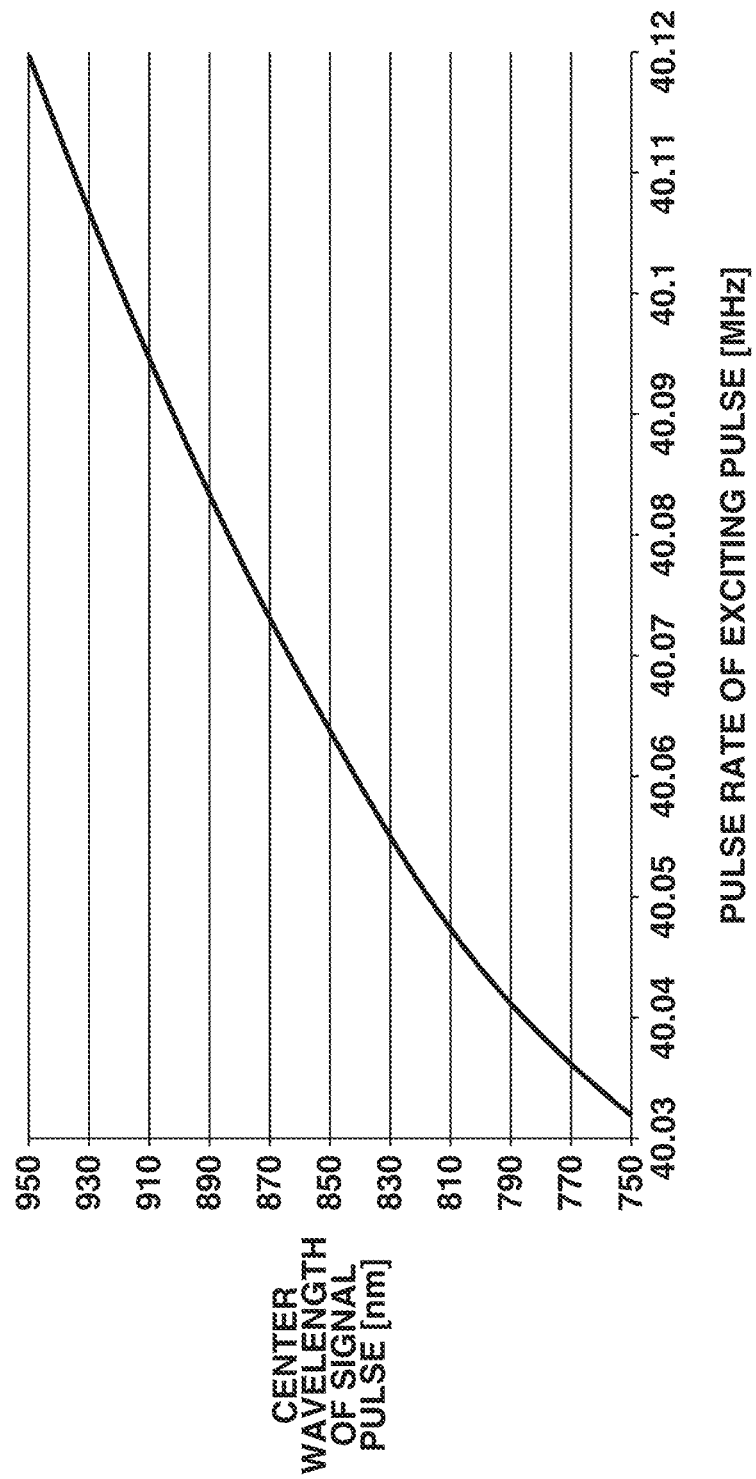
FIG. 11 is a graph illustrating the relationship between a change in a pulse rate of exciting pulsed light and a center wavelength of signal pulsed light capable of laser oscillation.

FIG. 11 illustrates a changing manner of the center wavelength of signal pulsed light that is capable of laser-oscillation, appearing when the pulse rate of exciting pulsed light is changed. FIG. 11 illustrates a graph in which the axis of ordinate indicates $\lambda$ in formula (8), and the axis of abscissa indicates $f_c$ in formula (8). Here, L=50 m, N=10, and a value of a general optical fiber (PM980-XP made by Nufern Inc.) is used as $n(\lambda)$. Generally, a refractive index n in the optical oscillator is dependent on a wavelength, so that the wavelength dispersion of the overall optical oscillator is not zero. Therefore, the oscillation frequency of light transmitted through the optical oscillator changes depending on the wavelength of the light. Hence, the center wavelength of signal pulsed light that is capable of oscillation changes in a nonlinear manner as illustrated in FIG. 11, depending on the pulse rate of exciting pulsed light.

FIG. 10 and FIG. 11 will be compared with each other. In FIG. 10, the center wavelength of the optical parametric gain changes nonlinearly, depending on the center wavelength of exciting pulsed light. In FIG. 11, the center wavelength of signal pulsed light, that is capable of oscillation, changes nonlinearly, depending on the pulse rate of exciting pulsed light. As is illustrated in FIG. 12A, where the center wavelength of the optical parametric gain is not coincident with the center wavelength of signal pulsed light satisfying formula (8), the light intensity of signal pulsed light varies, depending on the center wavelength of the signal pulsed light, when the center wavelength of signal pulsed light is changed.

Figure 12B:
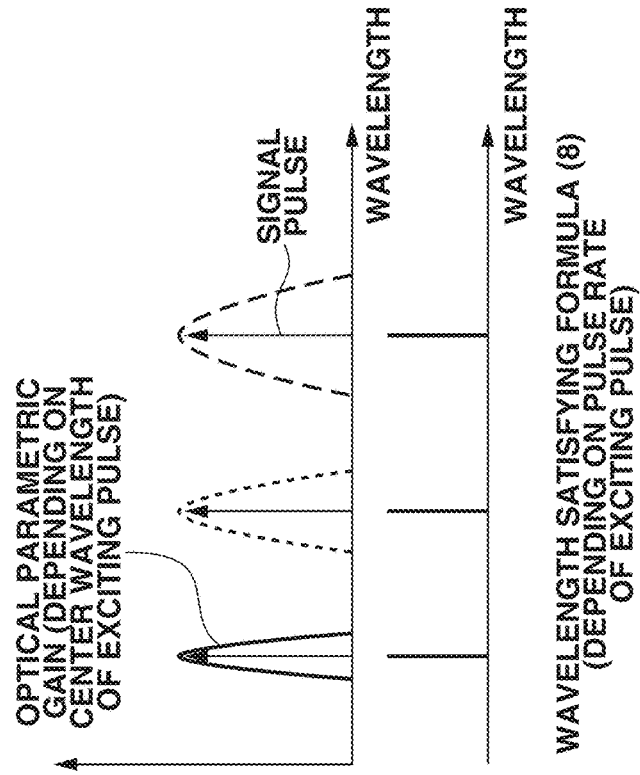
FIG. 12B is a view illustrating that light intensity of signal pulsed light is maintained constant irrespective of a center wavelength of signal pulsed light in the present invention.
Figure 12A:
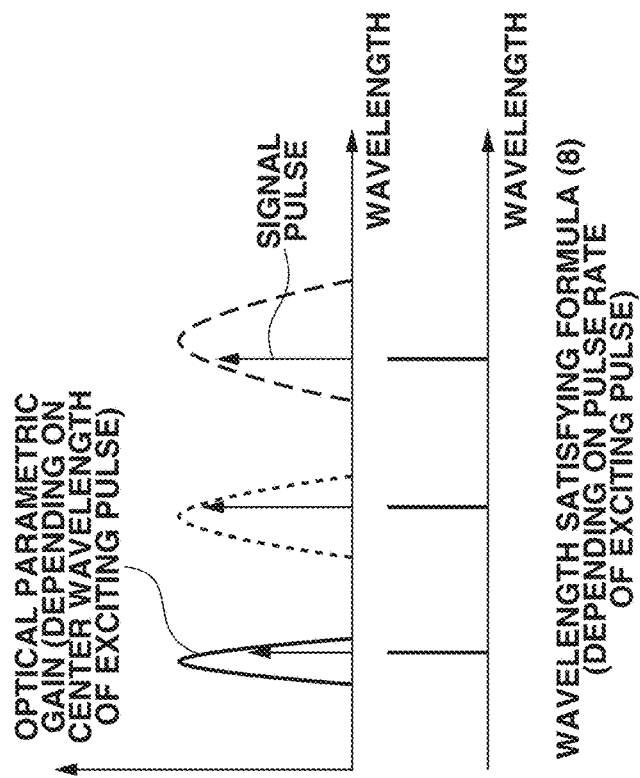
FIG. 12A is a view illustrating the phenomenon that light intensity of signal pulsed light varies depending on a center wavelength of signal pulsed light.

Therefore, according to the present invention, as illustrated in FIG. 12B, the center wavelength of the optical parametric gain is always made approximately coincident with the center wavelength of signal pulsed light satisfying formula (8) when the center wavelength of signal pulsed light is changed. As a result, it is possible to maintain the intensity of signal pulsed light constant since signal pulsed light always receives a constant optical parametric gain from the nonlinear optical medium even when the center wavelength of signal pulsed light changes.

Hereinafter, exemplary embodiments of light source apparatus and information acquisition apparatus according to the present invention will be described with reference to the drawings. However, the present invention is not limited to structures and the like of the exemplary embodiments. In the drawings, members designated by the same reference numerals are the same or corresponding members.

FIG. 1 illustrates the structure of a first exemplary embodiment. A seed laser 101 is a mode-locked fiber laser of a linear type including a mode locker of a saturable absorber mirror 1012, an Yb-doped fiber 1013 for supplying a gain, a chirp fiber Bragg grating (CFBG) 1014. The CFBG 1014 functions as both of dispersion compensator and output coupler. The Yb-doped fiber 1013 is excited when output light from a 980-nm semiconductor laser 1016 is guided using a frequency division multiplexing coupler 1015. Further, an optical delay device 1011 of a pulse rate adjustment portion for adjusting the cavity length is inserted in the seed laser 101. FIG. 17 illustrates a measurement result of a spectrum of pulsed light output from the seed laser 101. The center wavelength is 1032 nm, and the spectral full width at half maximum is 9 nm.

Figure 18:
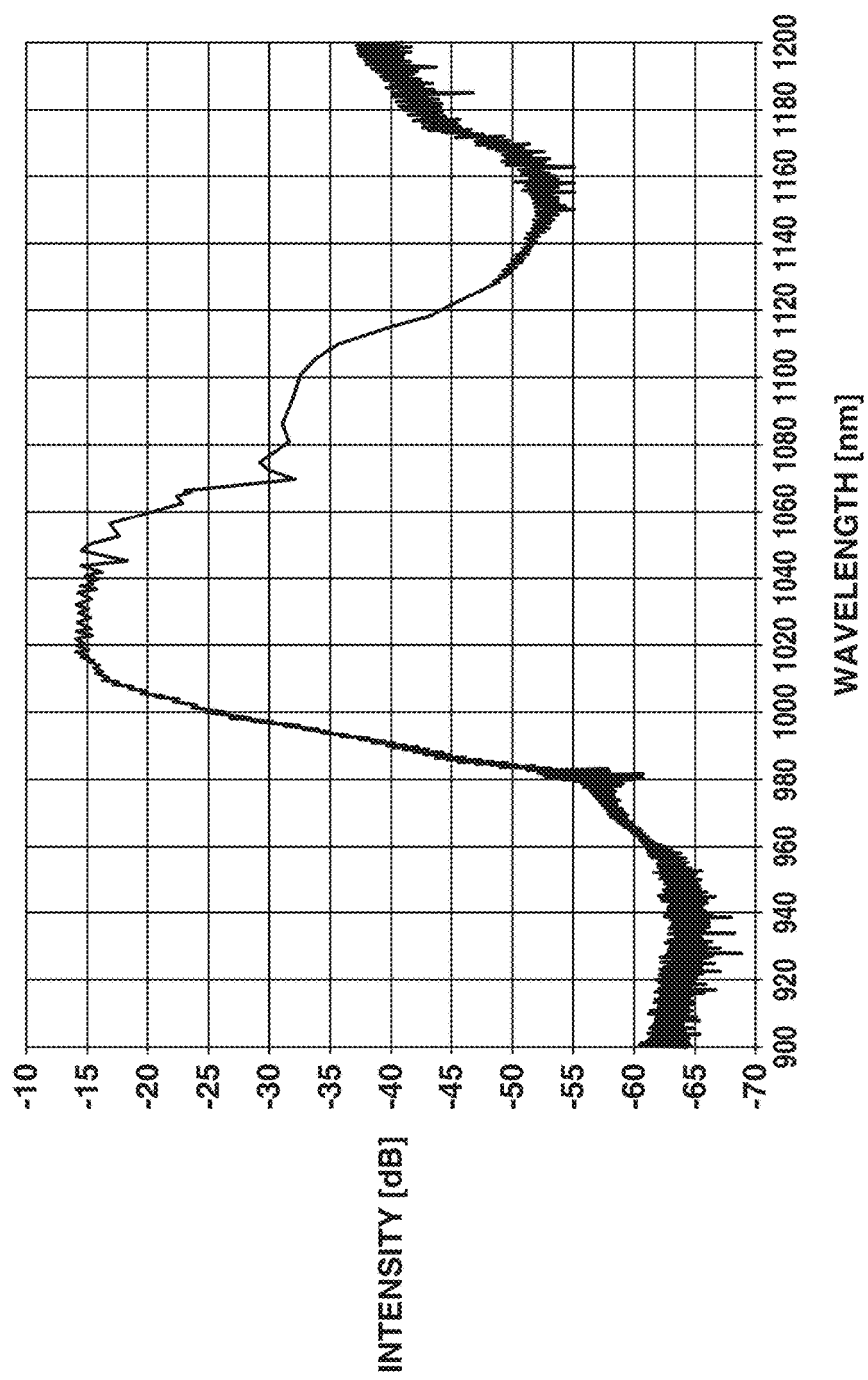
FIG. 18 is a graph illustrating a measurement result of spectrum as a result of broadened band region.

The pulsed light output from the seed laser 101 is transmitted through an isolator 102. Thereafter, the pulsed light is transmitted through the optical fiber amplifier 103 to be amplified. The optical fiber amplifier 103 includes a frequency division multiplexing coupler 1031, an Yb-doped fiber 1032, a 980-nm semiconductor laser 1033 of an exciting light source, and an isolator 1034. The optical fiber amplifier 103 is not limited to the above structure. A semiconductor optical amplifier can be used. The amplified pulsed light is transmitted through a photonic crystal fiber 104 (LMA-PM5, NKT made by Photonics Inc.), and a band region of its spectrum is broadened. As a result of the broadened band region, the spectrum of the pulsed light covers a region between 1015 nm and 1070 nm. FIG. 18 illustrates a measurement result of the above spectrum. The pulsed light with the broadened band region is divided into two halves of the light by a 1:1 fiber coupler 105.

One of the half-divided pulsed light is output from an emission end 119. The other one of the half-divided pulsed light is guided to a port P1 of a first polarization beam combiner 106. The pulsed light guided to the port P1 is transmitted through a slow axis of the optical fiber at a port P3. After that, the pulsed light is collimated and output from a fiber end 107. Thus, the pulsed light propagates through a wavelength tunable (selection) filter portion 108. In the wavelength tunable filter portion 108, the pulsed light is projected to and reflected by a galvano mirror 1081, and is projected to and reflected by a diffractive grating 1082. The diffractive grating 1082 reflects the diffraction pulsed light slightly downward. An optical axis of the diffraction pulsed light is adjusted by a D-type edge mirror 1083 and a mirror 1084, and the pulsed light is coupled to a fiber end 111. After transmission through the wavelength tunable filter portion 108, a spectral line width of the pulsed light is 0.5 nm. The spectral line width is preferably equal to or less than 1 nm. When the angle of the galvano mirror 1081 is changed, the wavelength of the pulsed light coupled to the fiber end 111 is changed. The wavelength tunable filter portion 108 is a spatial optical system in which half-wavelength plates 1085 and 1086 are respectively arranged at fiber ends 107 and 111 for adjustment of polarization. Instead of using the half-wavelength plate, angles of end faces of the fiber ends 107 and 111 can be rotated to control the polarization. Further, the wavelength tunable filter portion 108 can be replaced by a fiber filter of Fabry-Perot type or the like that is electrically controlled.

The pulsed light is coupled to the fiber end 111 along a slow axis of a polarization maintaining fiber. After the coupled pulsed light is transmitted through a 150 m long fiber 112 and then transmitted through an isolator 109, the coupled pulsed light is amplified by an Yb-doped fiber 113. The long fiber 112 gives chirp to the pulsed light, and the pulsed light is temporally broadened. The time width of the pulsed light is broadened to lower a peak power of the pulsed light, such that no unwanted nonlinear effect occurs in a FOPO described below. However, it is preferable that the pulse width is equal to or less than 1 µs. Further, the intensity of the pulsed light is increased by the Yb-doped fiber 113.

The pulsed light is guided to a port P3 of a second polarization beam combiner 114. Since the pulsed light is transmitted along the slow axis, the pulsed light is guided to a port P1 of a second polarization beam combiner 114. The pulsed light is transmitted through a WDM coupler 115, and coupled to the port P2 of the first polarization beam combiner 106. Here, it is possible in principle to guide the pulsed light to a port P2 of the second polarization beam combiner 114, and output the pulsed light into a WDM coupler 1171 for a FOPO. However, it is not preferable because the pulsed light passes through each device once, and hence its power becomes weak. Exciting light supplied from a 980-nm semiconductor laser 116 is input into the WDM coupler 115, and hence the Yb-doped fiber 113 is excited. The pulsed light coupled to the port P2 of the first polarization beam combiner 106 is transmitted along a fast axis of a port P3. As stated above, the pulsed light is transmitted through the fiber end 107, the wavelength tunable filter portion 108, the fiber end 111, the long fiber 112, the isolator 109, the Yb-doped fiber 113, and the second polarization beam combiner 114 in the named order. Here, the pulsed light is coupled to the port P3 of the second polarization beam combiner 114 along a fast axis, and hence the pulsed light is guided to a port P2. FIG. 19 illustrates a measurement result of spectrum of the pulsed light output from the port P2. By changing the angle of the galvano mirror 1081 in the wavelength tunable filter portion 108, the center wavelength of the pulsed light is changed at each interval of 10 nm in a range from 1020 nm to 1060 nm. A polarization beam splitter can be used as each of the first polarization beam combiner and the second polarization beam combiner.

The pulsed light with the adjusted center wavelength is guided to a FOPO 117 through the WDM coupler 1171 for the FOPO. Thereafter, the pulsed light is transmitted through the pump combiner 1172 and a double-clad Yb-doped fiber 1173. Owing to transmission through the double-clad Yb-doped fiber 1173, the intensity of the pump light is amplified. The double-clad Yb-doped fiber is excited by light output from a 980-nm exciting light source 1177. The amplified pump light is guided to a parametric gain fiber 1174 (NKT photonics, LMA-PM5), and hence the parametric gain is generated. A portion of signal light and a portion of idler light generated due to the parametric gain are divided by an output coupler 1175, and are taken out from a fiber end 110. The thus obtained portions are transmitted through a wavelength filter 118, and light in a desired wavelength band is taken out. In this exemplary embodiment, a short wavelength transmission filter for selecting light at a wavelength below 990 nm is used to take out light at a wavelength in a range between 780 nm and 980 nm. FIG. 20 illustrates a measurement result of spectrum of the above pulsed light. The wavelength variable range is from 780 nm to 980 nm. Further, FIG. 21 illustrates a graph in which output power at each wavelength known from the measurement result of spectrum is plotted. FIG. 22 illustrates a graph in which spectral width at each wavelength known from the measurement result of spectrum is plotted. The output power is 200 mW in the overall wavelength variable range, and the spectral width is 1 nm in the overall wavelength variable range. Pulsed light with the adjusted center wavelength is named first pulsed light, and signal light taken out by transmission through the wavelength filter is named second pulsed light. When the wavelength filter is changed, it is possible to employ the idler light as third pulsed light with a wavelength different from those of the first pulsed light and the second pulsed light.

Here, the signal light is light generated at a wavelength shorter than that of the pump light. The idler light is light generated at a wavelength longer than that of the pump light. Signal light or idler light that is not taken out is transmitted through a 50-m normal dispersion fiber 1176, and the polarization of this light is controlled by a polarization controller 1178. Thereafter, the cavity length of the FOPO is controlled by an optical delay device 1179, and the above light is coupled to the WDM coupler 1171 for the FOPO. The light is superimposed on the pulsed light repeatedly input into the FOPO. Hence, the light is given power due to the parametric gain in the parametric gain fiber 1174, and oscillation of the light occurs. In this exemplary embodiment, the normal dispersion fiber 1176 is not a polarization maintaining fiber, so that the polarization controller 1178 is inserted to adjust the polarization of the light. However, where a normal dispersion fiber that is a polarization maintaining fiber is used, the polarization controller 1178 can be omitted.

Further, in this exemplary embodiment, the repetition rate of the pump light is controlled such that a time point of the pump lights is made coincident with a time point of oscillation of light oscillated in the FOPO 117. The length of the fiber in the FOPO 117 is finely adjusted. It is hence possible to generate oscillation while the cavity length of the FOPO 117 is fixed without using the optical delay device 1179. Accordingly, the optical delay device 1179 can be removed. The polarization in the oscillator should be maintained constant. It is therefore necessary to use a polarization maintaining fiber or a polarization controller. Either can be used. Here, the structure for adjusting the cavity length is provided. Intrinsically, it is necessary to provide a portion for adjusting time points of incidence of the pump light and oscillation of light in the FOPO 117. This is achieved by a structure (for example, the optical delay device 1011) for adjusting the repetition rate of the seed light, or an adjusting structure for the optical oscillator of the FOPO 117.

Figure 2:
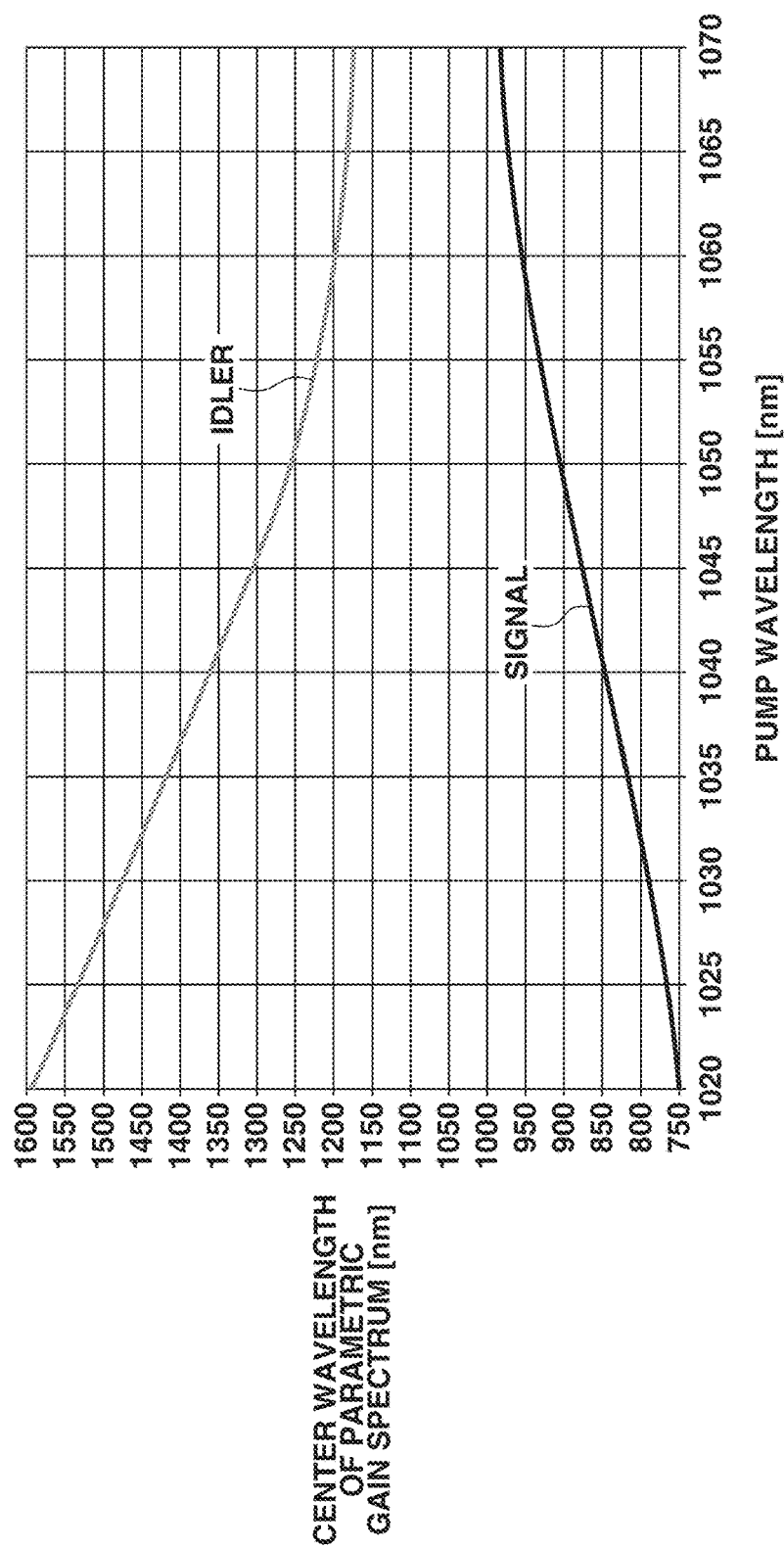
FIG. 2 is a graph illustrating the relationship between input pump light and a center wavelength of parametric gain.

The wavelength dispersion of the FOPO 117 is not zero. Hence, the oscillation frequency of light transmitted in the FOPO 117 varies depending on the wavelength. Therefore, the output wavelength fluctuates depending on the cavity length of the FOPO 117 and the repetition rate of the pump light input thereto. Further, the center wavelength of the parametric gain varies depending on the center wavelength of the input pump light. In this exemplary embodiment, center wavelength and repetition rate of the input pump light are adjusted to make the center wavelength of the parametric gain coincident with the oscillation wavelength of the FOPO 117. Hence, high output power can be obtained. The center wavelength of the parametric gain can be calculated from the above formula (3). FIG. 2 illustrates the center wavelength of the parametric gain calculated from the wavelength of the input pump light.

In this exemplary embodiment, light with a wavelength in a range between 780 nm and 980 nm is output. Accordingly, the center wavelength of the input pump light is controlled to be in a range between 1026 nm and 1069 nm. Further, in this exemplary embodiment, loss of light with a wavelength in the vicinity of 950 nm is large due to absorption by the double clad Yb-doped fiber 1173. Accordingly, the idler light with a wavelength in a range between 1510 nm and 1170 nm is resonated in the FOPO 117. Absorption of light with a wavelength in a range between 1510 nm and 1170 nm by the double clad Yb-doped fiber 1173 hardly occurs.

Figure 3:
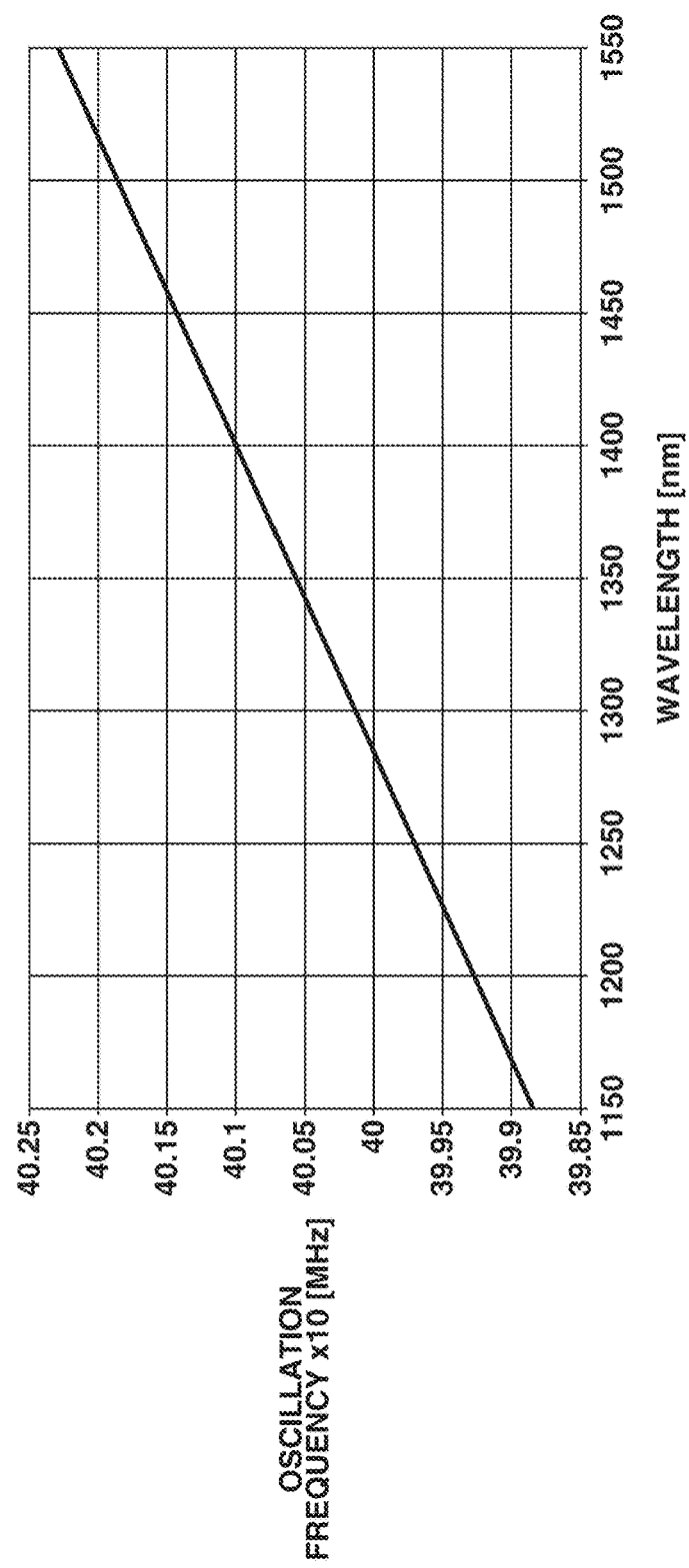
FIG. 3 is a graph illustrating the relationship between a wavelength and oscillation frequency in a FOPO.

FIG. 3 illustrates the repetition rate dependent on the wavelength of the idler light, that is calculated considering a type and length of the fiber used in the FOPO 117. The calculated frequency is multiplied by ten (10) to accord with the repetition rate of the seed light. This is an oscillation condition of the idler light. The frequency of the idler light should be an integer multiple of the repetition rate of the seed light. In this exemplary embodiment, considering the length of the fiber used in the FOPO 117, "ten times" is used, for example.

Figure 4:
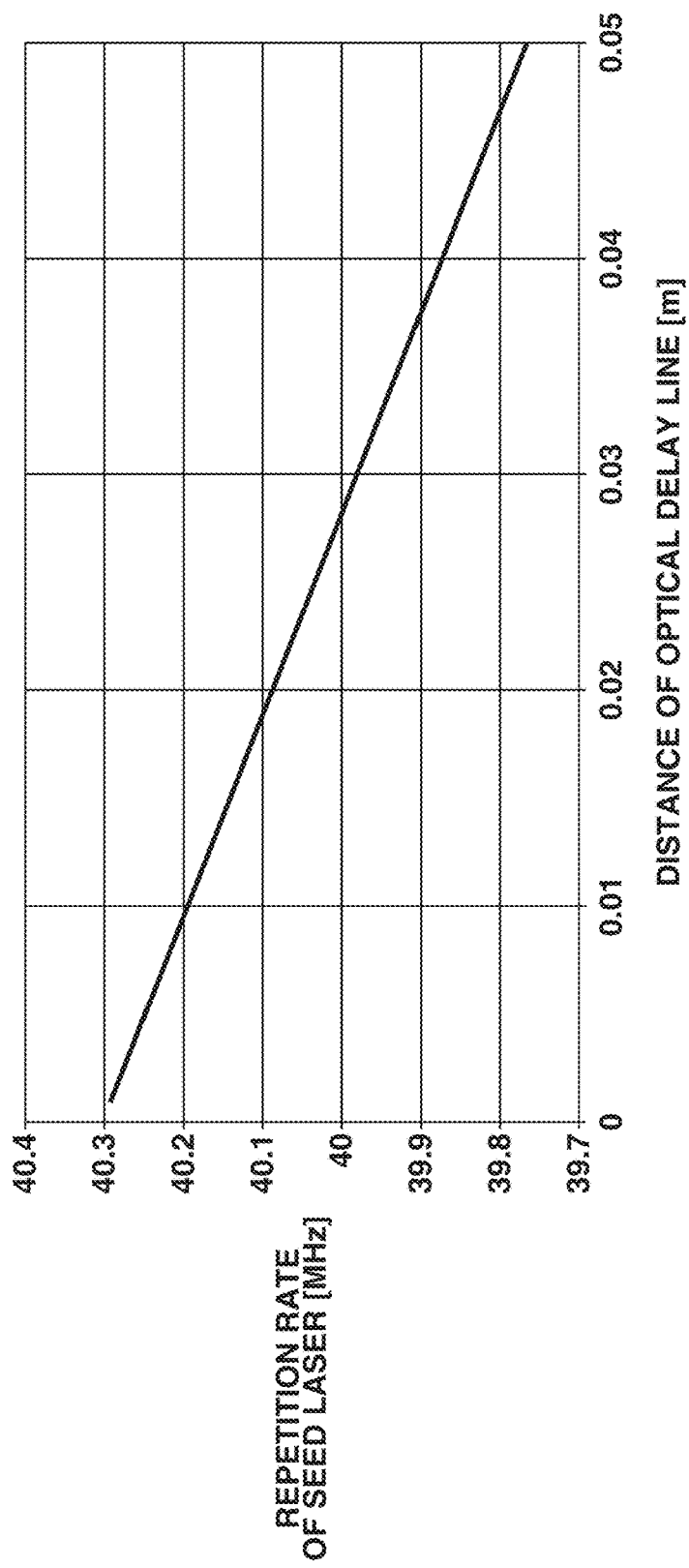
FIG. 4 is a graph illustrating the relationship between a repetition rate of a seed light source and a structure of an optical delay device.
Figure 5A:
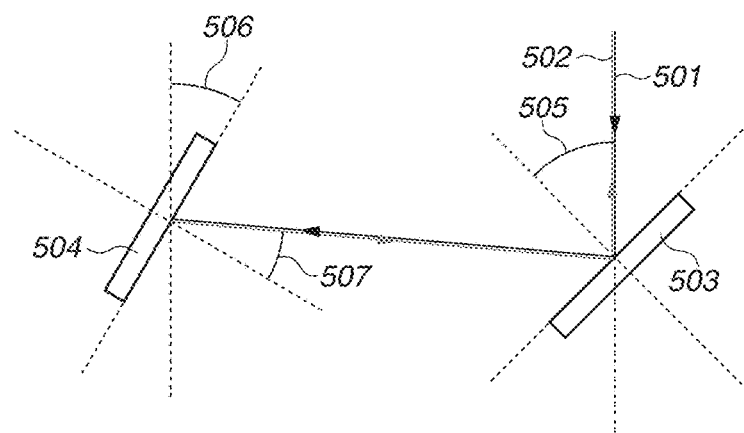
FIG. 5A is a view illustrating a structure of a wavelength tunable filter using a diffractive grating and a galvano mirror.
Figure 5B:
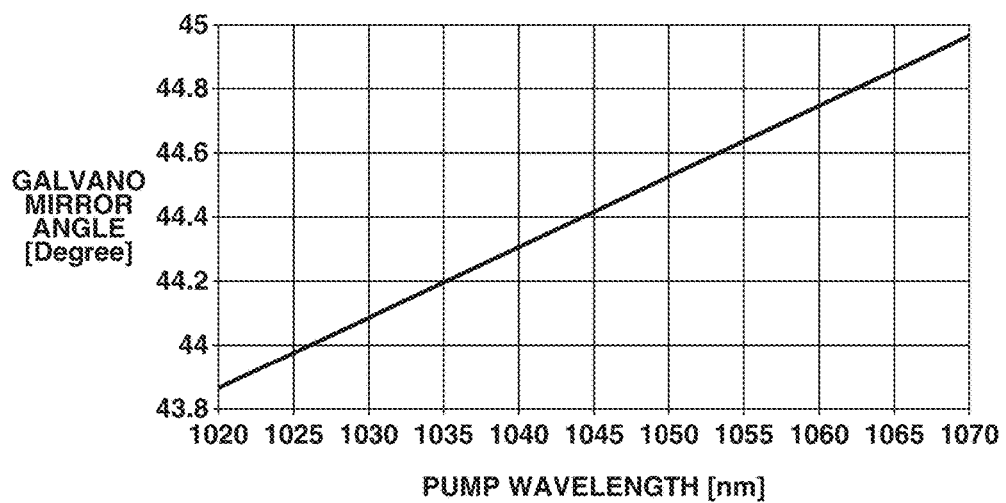
FIG. 5B is a graph illustrating the relationship between an output wavelength and an angle of the galvano mirror.

Calculation of a change in the repetition rate of the seed light is executed when a spatial length of the optical delay device 1011 is changed. FIG. 4 illustrates a result of the calculation. Further, FIG. 5B illustrates calculation results of the center wavelength of light to be coupled and the angle of a galvano mirror 503 in the case where a diffractive grating 504 with a reciprocal of the grating period of 1200/mm is used. As illustrated in FIG. 5A, when light 501 with a spectrum in a broad band region enters the galvano mirror 503, the light is incident on the diffractive grating 504 and frequency selection light 502 returns. Angular relationships can be represented by the following formulae (9) and (10):

$$\theta_{gi} = 2*\theta + \theta_g - \pi/2 \quad (9),$$

and $$\varphi = \theta_{gi} \quad (10),$$

where $\theta$ is an incident angle 505 of the incident light 501 on the galvano mirror 503, $\theta_g$ is an angle 506 of the diffractive grating 504 relative to a line parallel with an optical path of the incident light, $\theta_{gi}$ is an angle 507 of light entering the diffractive grating 504, and $\varphi$ is a reflection angle of light from the diffractive grating 504.

Further, from the angular relationships of the diffractive grating, the following formulae (11) can be obtained:

$$m\lambda N = \sin(\theta_{gi}) + \sin \varphi \quad (11),$$

and $$\theta(\lambda) = \frac{1}{2} * [\sin^{-1}(N\lambda/2) - \theta_g + \lambda/2] \quad (12),$$

where m is a diffraction order, $\lambda$ is a wavelength, and N is a reciprocal of the grating period of the diffractive grating 504. The following formula (12) can be obtained by using those formulae.

To summarize those results, as illustrated in FIG. 6A, it is possible to obtain the repetition rate and the center wavelength of the pump light, which are related to the wavelength of light output from the FOPO 117. Further, as illustrated in FIG. 6B, it is possible to obtain the spatial length of the optical delay device 1011 and the angle of the galvano mirror 1081, which are related to the wavelength of light output from the FOPO 117. In this exemplary embodiment, a computer 120, such as a personal computer (PC), of a control portion generates electrical signals based on the relationships illustrated in FIGS. 6A and 6B. Thus, the optical delay device 1011 and the galvano mirror 1081 are controlled. Further, electrical signals generated in the computer 120 vary over time according to relationships illustrated in FIGS. 6A and 6B such that the optical delay device 1011 and the galvano mirror 1081 are automatically controlled. Hence, a high-speed wavelength tunable light source with a high output can be obtained. The computer 120 is not limited to PC. A programmed controller, function generator or the like can be used.

An example of this exemplary embodiment will be described. To output desired signal light with a wavelength $\Lambda_1$, pump light with a center wavelength $\lambda_1$ is input to the oscillator of the FOPO 117. In this case, a repetition rate $f_1$ of the pump light with the center wavelength $\lambda_1$ is adjusted to such a value that causes the oscillation wavelength of the FOPO 117 to be approximately coincident with a peak wavelength of the FOPO 117. The peak wavelength is determined by the center wavelength $\lambda_1$ of pump light. The center wavelength $\lambda_1$ and the repetition rate $f_1$ can be set by calculating an optimum combination thereof based on the above result. Alternatively, the center wavelength $\lambda_1$ and the repetition rate $f_1$ can be set by using a memory unit (not shown) that stores a table of a correspondence relation thereof obtained beforehand. In the present exemplary embodiment, the center wavelength $\lambda_1$ can be changed by changing an angle of the galvano mirror 1081. The repetition rate $f_1$ can be changed through adjusting the length of an optical path by the optical delay device 1011.

To change the wavelength of the signal light to a wavelength $\Lambda_2$ that is larger than the wavelength $\Lambda_1$, increase in the angle of the galvano mirror 1081 brings the wavelength $\lambda_1$ of the pump light to the wavelength $\lambda_2$ that is larger than the wavelength $\lambda_1$. As a result of increase in the wavelength of the pump light, the peak wavelength of the FOPO 117 to which the pump light is input is changed. Then, the optical delay device 1011 is controlled such that the thus-changed peak wavelength of the FOPO 117 is approximately coincident with the oscillation wavelength of the FOPO 117. More specifically, the repetition rate of the pump light that determines a value of the oscillation wavelength of the FOPO 117 is changed to $f_2$ that is smaller than $f_1$. Hence, the peak wavelength of the FOPO 117 is made approximately equal to the oscillation wavelength of the FOPO 117. To decrease the repetition rate of the pump light, the length of an optical path of the optical delay device 1011 is decreased. The angle of t galvano mirror 1081 and the length of an optical path of the optical delay device 1011 are controlled by the controller (computer) 120 based on a correspondence relation thereof stored in a memory unit (not shown). The galvano mirror 1081 and the optical delay device 1011 can be controlled by a single controller 120, or by respective controllers.

Further, the following control can also be executed. That is, the angle of the galvano mirror 1081 and the length of an optical path of the optical delay device 1011 are calculated by a calculation unit (not shown) according to a wavelength of the signal light to be output, and the controller 120 controls them based on a result of the calculation. For example, initially, a center wavelength of gain of the FOPO 117 is calculated from a center wavelength of exciting pulse light (including pump light) which is to be input to the FOPO 117, using formula (5). Then, the refractive index of the overall FOPO 117 is calculated from the thus-calculated center wavelength of gain of the FOPO 117. The pulse rate of the exciting pulse light is calculated from the calculated refractive index, using formula (8). The pulse rate (repetition rate) of the exciting pulse light is adjusted to the calculated value.

A unit for changing the angle of the galvano mirror 1081 is not limited to a specific one. It is possible to use a unit for changing the angle by rotation of a motor. Further, a unit for changing the length of an optical path by using the optical delay device 1011 is not limited to a specific one. It is possible to use a unit such as a linear motor for moving a mirror in a translational direction. A piezoelectric element can be used where an amount of change in the length of an optical path is small, or where the length of an optical path is changed at high speed.

A second exemplary embodiment has the structure described in the first exemplary embodiment. In the second exemplary embodiment, a relationship between the repetition rate and the center wavelength of pump light, which are related to the wavelength of output from the FOPO 117, is actually measured. Based on measured values, the wavelength of pulsed light output from the FOPO 117 is controlled.

Figure 7:
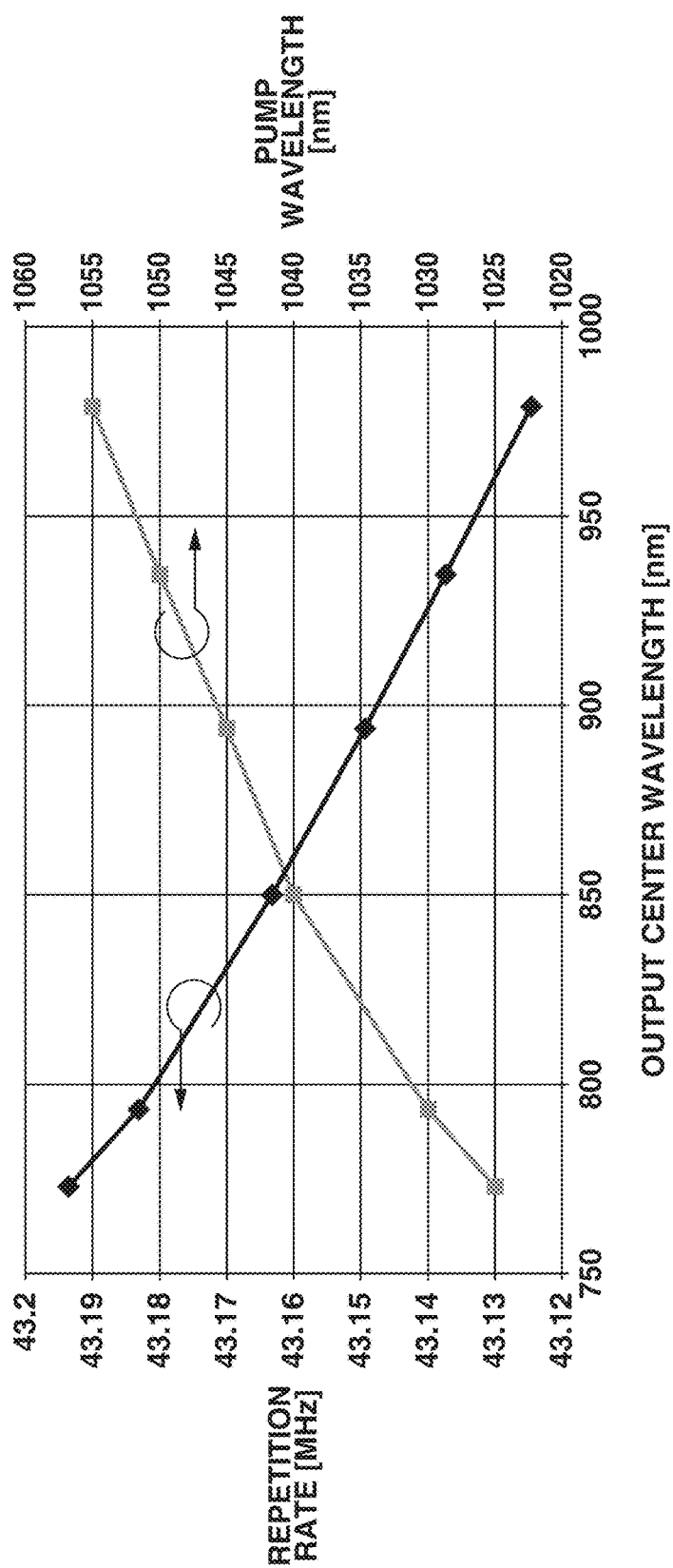
FIG. 7 is a graph illustrating a measured relationship among an output wavelength of the FOPO, a repetition rate, and a pump light wavelength.

FIG. 7 illustrates measured values indicating the relationship between repetition rate and center wavelength of the pump light, and the wavelength of output from the FOPO 117. The optical delay device for controlling the repetition rate and the galvano mirror for controlling the center wavelength are controlled by electrical signals output from the computer such that the relationship shown in FIG. 7 can be satisfied. Further, electrical signals generated in the computer vary over time according to the relationship illustrated in FIG. 7, and hence the optical delay device and the galvano mirror are automatically controlled. Thus, a high-speed wavelength tunable light source with a high output can be realized. A programmed controller, function generator or the like can be used in place of the computer. Here, instead of using calculated values, the control is performed using values actually measured.

Figure 8:
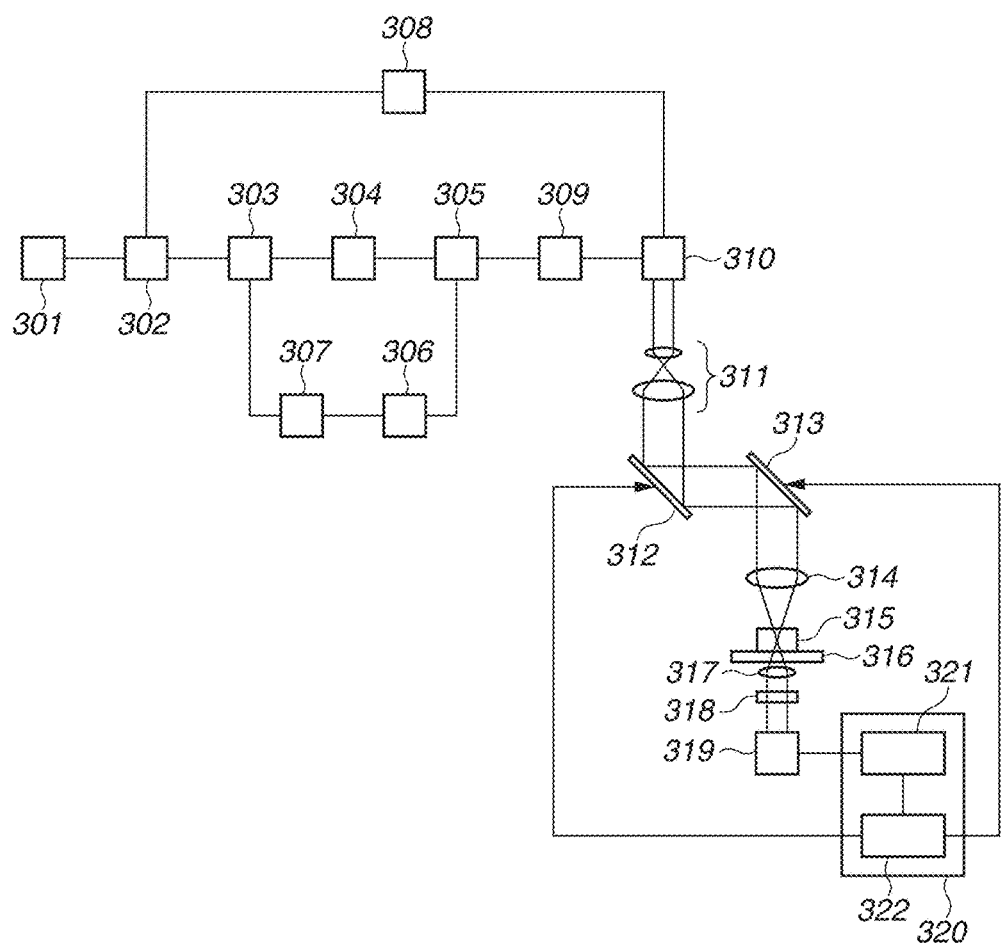
FIG. 8 is a schematic view illustrating a light source apparatus according to a third exemplary embodiment of the present invention.

FIG. 8 illustrates an information acquisition apparatus according to a third exemplary embodiment. In this exemplary embodiment, SRS imaging is executed using the light source apparatus described in the first exemplary embodiment. A microscope for SRS imaging (SRS microscope) is described as an example of apparatus.

The SRS imaging utilizes the phenomenon of stimulated Raman scattering that when pump light is incident on a substance, Stokes ray is amplified due to interaction between the pump light and the Stokes ray. Thus, the molecular vibration imaging is executed. More specifically, under a condition that the intensity of one of two pulsed light beams with wavelengths different from each other, i.e., Stokes ray, is modulated, an object is synchronously irradiated with the two pulsed light beams. When a frequency difference between frequencies of the two pulsed light beams coincides with the molecular vibration frequency of molecules of the object, the stimulated Raman scattering occurs and hence the intensity-modulated Stokes ray is amplified. Then, according to the intensity modulation of the Stokes ray, the intensity of the pulsed light without any intensity modulation, i.e., the pump light, is modulated. It is possible to execute the molecular vibration imaging of the object by detecting the intensity modulation of the pump light emitted from the object due to the stimulated Raman scattering. Further, when the center wavelength of the pulsed light is changed to change the frequency difference between the two pulsed light beams, the frequency difference can be made coincident with one of molecular vibration frequencies of a variety of molecules. Hence, a signal specific to a molecular group constituting the object can be acquired.

The exciting pulsed light (first pulsed light) emitted from a light source 301 is divided into two light beams by a light branch portion 302, and one of the two light beams is modulated by an optical modulator 308. The modulated light is used as a Stokes ray for the SRS microscope. The light source 301 corresponds to a portion other than the FOPO 117 illustrated in FIG. 1, and portions designated by reference numerals 303 to 307 in FIG. 8 correspond to the FOPO 117 in FIG. 1. The other light is input into a nonlinear optical medium 304 through a light branch portion 303, and hence second pulsed light (signal pulsed light) with the center wavelength different from that of the first pulsed light generated. An optical fiber with high nonlinear factor, such as a photonic crystal fiber and a tapered fiber, can be preferably used as the nonlinear optical medium 304. The generated second pulsed light is input into a first waveguide 306 and a second waveguide 307 through a light branch unit 305, and is again input into the nonlinear optical medium 304. Thus, the second pulsed light is circulated through the oscillator to be oscillated. A spectral line width of oscillated light is narrowed. The oscillated second pulsed light is taken out through a band pass filter 309. The second pulsed light selected through the band pass filter 309 is used as pump light for the SRS microscope.

The Stokes ray and pump light are combined by a light combiner 310 that is a light combining portion, and the object is irradiated with the combined light. As the light combiner 310 for combining a plurality of pulsed light beams with center wavelengths different from each other, a light coupler, a diffractive grating, a prism or the like can be used. The Stokes ray and the pump light combined each other are condensed on the object 315 settled on a stage 316 through a beam expander 311, an X-scan mirror 312, a Y-scan mirror 313, and an object lens 314.

In a minute region on the object 315 at a center point of light collection of the object lens 314, stimulated Raman scattering occurs due to molecular vibration molecules, and hence intensities of the pump light and the Stokes ray are changed. In a region outside the center point of light collection, no stimulated Raman scattering occurs, so that no intensity changes of the pump light and the Stokes ray appears. The size of a light spot projected on the object 315 becomes smaller as NA of the object lens 314 increases. Accordingly, the size of the minute region where the stimulated Raman scattering occurs decreases.

The pump light has the modulated intensity due to stimulated Raman scattering appearing in the minute region at the center point of light collection. The pump light with the modulated intensity passes through a light collection lens 317 and a band pass filter 318, and is input into a light receiving device 319. The pump light is detected as the SRS signal, and is acquired by an information acquisition portion 320 as image signal and the like.

Generally, since a Raman scattering cross section σ of molecules is small, a change in the intensity of pump light due to the stimulated Raman scattering is weak. Therefore, when the SRS signal is detected from the change in the intensity of pump light, the SRS signal is sometimes buried in noise component and the like. In this exemplary embodiment, an information acquisition portion 320 provided with a synchronous detector 321 and a control portion 322 is used, and the intensity modulation of the pump light received by the light receiving device 319 and converted into an electrical signal is detected synchronously with the modulation frequency of the optical modulator. Thus, the molecular vibration imaging or the like of the object 315 is obtained. When the signal synchronously detected is amplified, the SRS signal can be detected with a high sensitivity.

As the synchronous detector 321, a lock-in amplifier, a fast Fourier transform (FFT) analyzer or the like can be used. Compared with the lock-in amplifier, the FFT analyzer can detect the SRS signal at a higher speed. FIG. 8 illustrates a structure in which the synchronous detector 321 is provided separately from the control portion 322. However, it is possible to use an information acquisition portion 320 in which the synchronous detector 321 and the control portion 322 are combined in one unit. As such an example, a computer provided with CPU used as the control portion 322 can be selected. This computer has a built-in application with a synchronous detection function.

When an X-scan mirror 312 is driven, the light collection point is scanned in an X-direction in the object 315. When a Y-scan mirror 313 is driven, the light collection point is scanned in a Y-direction perpendicular to the X-direction in the object 315. Accordingly, when the light collection point is scanned on the object 315 by the X-scan mirror 312 and the Y-scan mirror 313, a two-dimensional image can be acquired. Further, a three-dimensional image can be obtained in the following manner. After a two-dimensional scan is performed, the stage 316 is moved to displace the light collection point by a predetermined distance in an optical-axis direction. The two-dimensional scan is similarly repeated to obtain the three-dimensional image of the object 315.

Further, after a first two-dimensional scan or three-dimensional scan is executed, the center wavelength of the light source 301 is changed to change the frequency difference between two wavelengths of the pump light and the Stokes ray. Hence, the frequency difference can be made coincident with one of a variety of molecular vibration frequencies of molecules contained in the object 315. It is thereby possible to obtain the two-dimensional or three-dimensional molecular vibration image or information. Here, the center wavelength of the light source can be controlled based on the relationship illustrated in FIG. 6 or FIG. 7 by using electrical signals for automatic control output from the computer or programmed controller. It is hence possible to vary the wavelength at high speed. Alternatively, after information according to a variety of molecular vibration frequencies is acquired at a certain point by changing the wavelength at high speed, the point is moved to a next point and information according to a variety of molecular vibration frequencies is again acquired. Such information acquisition can be repeatedly executed. Thus, it is also possible to obtain the two-dimensional or three-dimensional molecular vibration image.

In this exemplary embodiment, a pulse width of the pulsed light emitted from the light source apparatus using the SRS microscope is preferably equal to or less than 1 ns. The pulse width is more preferably equal to or less than 100 ps. Reasons therefor are that the peak intensity of the pulsed light increases as the pulse width becomes narrower, and that presence or absence of the nonlinear effect generated in the object 315 can be detected with high precision. Further, the pulse rate of pulsed light emitted from the light source 301 is preferably equal to or more than 1 MHz, and equal to or less than 1 GHz. Reasons therefor are that the former (over 1 MHz) is preferable in the light of constraint of the measurement speed realistically required for the SRS microscope, and the latter (under 1 GHz) is preferable in the light of constraint of thermal destruction appearing in the object 315.

Further, since the SRS microscope can be preferably used for observation of biological tissue, it is preferable that pulsed light emitted from the light source apparatus has a wavelength that has small reflection, absorption, and scattering factor by a living body, and that can be easily transmitted through the living body. Accordingly, the center wavelength of pulsed light emitted from the light source apparatus is preferably equal to or more than 300 nm and equal to or less than 1500 nm. It is particularly preferable that the center wavelength is equal to or more than 700 nm and equal to or less than 1300 nm. For example, the light source 301 preferably includes a mode synchronous Yb-doped (ytterbium-doped) fiber laser.

As described above, in the SRS microscope of this exemplary embodiment, the spectral line width of signal pulsed light can be maintained constant irrespective of the center wavelength of the signal pulsed light. Therefore, resolution of Raman spectrum obtained from the object can be maintained constant. Further, compared with a conventional SRS microscope apparatus, downsizing and cost reduction of the light source apparatus can be attained. Consequently, downsizing and cost reduction of the overall SRS microscope apparatus can be achieved. In the conventional SRS microscope apparatus, a solid-state laser is used. In contrast thereto, each light source in the above exemplary embodiments is constituted of a fiber laser. By using such light source, downsizing and cost reduction of the SRS microscope apparatus can be attained. Further, in an information acquisition apparatus according to another aspect of the present invention, signal intensities of various spectral spectra, such as Raman spectrum, obtained from the object can be maintained constant.

In this exemplary embodiment, the SRS microscope is described as the information acquisition apparatus in which the object is irradiated with two pulsed light beams, and at least one of light reflected by the object, light transmitted through the object, and light generated in the object is detected to acquire information of the object. However, the apparatus is not limited thereto. Similarly to this exemplary embodiment, the light source apparatus of the first or second exemplary embodiment can be used in an information acquisition apparatus for obtaining various spectral information, such as CARS microscope, fluorescence microscope, and endoscope.

According to one aspect of the present invention, when the center wavelength of signal pulsed light is changed, the light intensity of signal pulsed light can be maintained constant irrespective of the center wavelength thereof.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2016-177198, filed Sep. 12, 2016, and No. 2017-146079, filed Jul. 28, 2017, which are hereby incorporated by reference herein in their entirety.

What is claimed is:

1. A light source apparatus comprising:
   a light source portion configured to emit first pulsed light;
   an optical oscillator including a nonlinear optical medium for generating second pulsed light with a wavelength different from a wavelength of the first pulsed light upon incidence of the first pulsed light on the medium;
   a light branch portion configured to branch and output the second pulsed light;

a light combining portion configured to guide the second pulsed light to the optical oscillator and guide the first pulsed light to the optical oscillator;

a center wavelength adjustment portion configured to adjust a center wavelength of the first pulsed light; and a pulse rate adjustment portion configured to perform adjustment such that a pulse rate of the first pulsed light coincide with an integer multiple of a free spectral interval of the optical oscillator at a center wavelength of the second pulsed light, wherein a center wavelength of a nonlinear gain generated by the nonlinear optical medium is made approximately coincident with the center wavelength of the second pulsed light.

2. The light source apparatus according to claim 1, wherein the pulse rate adjustment portion includes a portion for adjusting a cavity length of the optical oscillator.

3. The light source apparatus according to claim 1, wherein the pulse rate adjustment portion includes a portion for adjusting the pulse rate of the first pulsed light.

4. The light source apparatus according to claim 3,
wherein the light source portion includes an optical oscillator with a nonlinear optical medium, and
wherein a portion for adjusting the pulse rate of the first pulsed light includes an optical delay device for adjusting a cavity length of the optical oscillator in the light source portion.

5. The light source apparatus according to claim 1, wherein the optical oscillator, including the nonlinear optical medium for generating the second pulsed light, generates a third pulsed light with a wavelength different from a wavelength f the first pulsed light and a wavelength of the second pulsed light.

6. The light source apparatus according to claim 1, wherein the nonlinear optical medium for generating the second pulsed light includes a photonic crystal fiber.

7. The light source apparatus according to claim 1, wherein the center wavelength adjustment portion is a frequency selection filter portion including a diffractive grating.

8. The light source apparatus according to claim 1, wherein a spectral line width of the first pulsed light equal to or less than 1 nm.

9. The light source apparatus according to claim 1, wherein a pulse width of the first pulsed light is equal to or less than 1 μs.

10. The light source apparatus according to claim 1, further comprising a control portion for controlling the center wavelength adjustment portion and the pulse rate adjustment portion by electrical signals.

11. An information acquisition apparatus comprising:
a light source apparatus according to claim 1; and
a light receiving device configured to receive at least one of light reflected by an object, light transmitted through the object, and light generated in the object, when two pulsed light beams with center wavelengths different from each other is emitted from the light source apparatus and the object is irradiated with the two pulsed light beams.

12. The information acquisition apparatus according to claim 11, wherein one of the two pulsed light beams is the second pulsed light, and the other of the two pulsed light beams is the first pulsed light that is modulated.

13. The information acquisition apparatus according to claim 11, wherein pulse rates of the two pulsed light beams are respectively equal to or more than 1 MHz and equal to or less than 1 GHz.

14. The information acquisition apparatus according to claim 11, further comprising an information acquisition portion configured to acquire light received by the light receiving portion as an electrical signal,
wherein the information acquisition portion includes a synchronous detector for acquiring a signal synchronously with a modulation of the light received by the light receiving device.

15. A light source apparatus comprising:
a light source portion configured to emit first pulsed light;
an optical oscillator including a nonlinear optical medium for generating second pulsed light with a wavelength different from a wavelength of the first pulsed light upon incidence of the first pulsed light on the medium;
a light branch portion configured to branch and output the second pulsed light;
a light combining portion configured to guide the second pulsed light to the optical oscillator and guide the first pulsed light to the optical oscillator;
a center wavelength adjustment portion configured to adjust a center wavelength of the first pulsed light; and
a pulse rate adjustment portion configured to perform adjustment such that a pulse rate of the first pulsed light coincides with an integer multiple of a free spectral interval of the optical oscillator at a center wavelength of the second pulsed light.

16. The light source apparatus according to claim 15,
wherein a center wavelength of a nonlinear gain generated by the nonlinear optical medium is made approximately coincident with the center wavelength of the second pulsed light.

17. The light source apparatus according to claim 15,
wherein a wavelength at which a nonlinear optical medium has a peak gain is made approximately coincident with the center wavelength of the second pulsed light.

* * * * *